(12) United States Patent
Milne et al.

(10) Patent No.: US 8,765,963 B2
(45) Date of Patent: *Jul. 1, 2014

(54) FATTY ACID NIACIN CONJUGATES AND THEIR USES

(75) Inventors: Jill C. Milne, Brookline, MA (US); Michael R. Jirousek, Cambridge, MA (US); Jean E. Bemis, Arlington, MA (US); Chi B. Vu, Arlington, MA (US); Amal Ting, Newton, MA (US)

(73) Assignee: Catabasis Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/451,217

(22) Filed: Apr. 19, 2012

(65) Prior Publication Data

US 2012/0264791 A1  Oct. 18, 2012

Related U.S. Application Data

(63) Continuation-in-part of application No. 12/872,555, filed on Aug. 31, 2010, now Pat. No. 8,304,551.

(60) Provisional application No. 61/478,091, filed on Apr. 22, 2011, provisional application No. 61/238,903, filed on Sep. 1, 2009, provisional application No. 61/308,524, filed on Feb. 26, 2010, provisional application No. 61/310,952, filed on Mar. 5, 2010.

(51) Int. Cl.
  *C07D 211/72*  (2006.01)
  *A61K 31/44*  (2006.01)
  *C07D 213/82*  (2006.01)

(52) U.S. Cl.
  CPC .............. *C07D 213/82* (2013.01); *A61K 31/44* (2013.01)
  USPC .......................................... 546/316; 514/355

(58) Field of Classification Search
  CPC ................................................... C07D 213/82
  See application file for complete search history.

(56) References Cited

U.S. PATENT DOCUMENTS

| 4,169,923 A | 10/1979 | Ferruti et al. |
| 4,619,938 A | 10/1986 | Suwabe et al. |
| 4,794,115 A | 12/1988 | Takahashi et al. |
| 6,015,821 A | 1/2000 | Horrobin et al. |
| 6,562,995 B1 | 5/2003 | Lan-Hargest et al. |
| 6,649,633 B2 | 11/2003 | Chambers et al. |
| 6,956,077 B1 | 10/2005 | Akiyama et al. |
| 7,226,930 B2 | 6/2007 | Hopper et al. |
| 7,560,473 B2 | 7/2009 | Wang et al. |
| 8,304,551 B2 | 11/2012 | Milne et al. |
| 2006/0039962 A1 | 2/2006 | Heldman et al. |
| 2006/0105021 A1 | 5/2006 | Steele et al. |

FOREIGN PATENT DOCUMENTS

| JP | 62-106080 | 5/1987 |
| JP | 62-106083 | 5/1987 |
| JP | 62-258362 | 11/1987 |
| JP | 01-121253 | 5/1989 |
| WO | WO 96/34855 | 11/1996 |
| WO | WO 96/34858 | 11/1996 |
| WO | WO 00/08015 | 2/2000 |

OTHER PUBLICATIONS

English language abstract for JP 62-106080 (2 pages), 1987.
English language abstract for JP 62-106083 (1 page), 1087.
English language abstract for JP 01-121253 (1 page), 1989.
English language abstract for JP 62-258362 (2 pages), 1987.
Keusgen et al., "Sulfoquinovosyl Diacylglycerols from the Alga Heterosigma carterae," Lipids, Springer, DE, vol. 32, No. 10, Jan. 1, 1997 (12 pages).
Seki, et al., "Studies on Hypolipidemic Agents. I. Synthesis and Pharmacological Properties of Nicotinic Acid-Ethanolamine Derivatives," Chem. Pharm. Bull., 1983, 11 pages.
English language abstract for JP 62-106083 (1 page), 1987.
International Search Report and Written Opinion for International Application No. PCT/US2010/047262, mailed Oct. 22, 2010.
Silverman, R., "The Organic Chemistry of Drug Design and Drug Action," 2004, Elsevier, pp. 29-32.

*Primary Examiner* — Heidi Reese
(74) *Attorney, Agent, or Firm* — Cooley LLP

(57) ABSTRACT

The invention relates to fatty acid niacin conjugates; compositions comprising an effective amount of a fatty acid niacin conjugate; and methods for treating or preventing an metabolic disease comprising the administration of an effective amount of a fatty acid niacin conjugate.

40 Claims, 2 Drawing Sheets

* $p < 0.005$,  $p < 0.01$, * $p < 0.05$ by 1-way ANOVA with Dunnett's Post test

FATTY ACID NIACIN CONJUGATES AND THEIR USES

PRIORITY

This application claims the benefit of U.S. Provisional Application No. 61/478,091 filed Apr. 22, 2011 and is a continuation-in-part of U.S. Non-Provisional application Ser. No. 12/872,555 filed Aug. 31, 2010, which claims priority to U.S. Provisional Application No. 61/238,903, filed Sep. 1, 2009, U.S. Provisional Application No. 61/308,524, filed Feb. 26, 2010, and U.S. Provisional Application No. 61/310,952, filed Mar. 5, 2010. The entire disclosures of those applications are relied on and incorporated into this application by reference.

FIELD OF THE INVENTION

The invention relates to fatty acid niacin conjugates; compositions comprising an effective amount of a fatty acid niacin conjugate; and methods for treating or preventing a metabolic disease comprising the administration of an effective amount of a fatty acid niacin conjugate.

BACKGROUND OF THE INVENTION

Oily cold water fish, such as salmon, trout, herring, and tuna are the source of dietary marine omega-3 fatty acids, eicosapentaenoic acid (EPA) and docosahexaenoic acid (DHA) being the key marine derived omega-3 fatty acids. Both niacin and marine omega-3 fatty acids (EPA and DHA) have been shown to reduce cardiovascular disease, coronary heart disease, atherosclerosis and reduce mortality in patients with dyslipidemia, hypercholesterolemia, or Type 2 diabetes, and metabolic disease. Niacin at high dose (1.5 to 4 grams per day) has been shown to improve very low-density lipoprotein ("VLDL") levels through lowering Apolipoprotein B ("ApoB") and raising high density lipoprotein ("HDL") through increasing Apolipoprotein A1 ("ApoA1") in the liver. Niacin can also inhibit diacylglycerol acyltransferase-2, a key enzyme for TG synthesis (Kamanna, V. S.; Kashyap, M. L. *Am. J. Cardiol.* 2008, 101 (8A), 20B-26B). Unfortunately, niacin has many actions outside of the liver that detract from its therapeutic utility. The most common side effect of niacin is flushing, which can limit the dose a patient can tolerate. Flushing is thought to occur through the GPR109 receptor in the vasculature. Non-flushing niacin derivatives have been disclosed in WO 2008/016968, and these derivatives are reported to potentially have the same beneficial effect on raising HDL as niacin while displaying a lesser degree of flushing.

Omega-3 fatty acids (such as DHA and EPA) have been shown to improve insulin sensitivity and glucose tolerance in normoglycemic men and in obese individuals. Omega-3 fatty acids have also been shown to improve insulin resistance in obese and non-obese patients with an inflammatory phenotype. Lipid, glucose, and insulin metabolism have been show to be improved in overweight hypertensive subjects through treatment with omega-3 fatty acids. Omega-3 fatty acids (EPA/DHA) have also been shown to decrease triglycerides and to reduce the risk for sudden death caused by cardiac arrhythmias in addition to improve mortality in patients at risk of a cardiovascular event. Omega-3 fatty acids have also been taken as part of the dietary supplement portion of therapy used to treat dyslipidemia.

Both DHA and EPA are characterized as long chain fatty acids (aliphatic portion between 12-22 carbons). Medium chain fatty acids are characterized as those having the aliphatic portion between 6-12 carbons. Lipoic acid is a medium chain fatty acid found naturally in the body. It plays many important roles such as free radical scavenger, chelator to heavy metals and signal transduction mediator in various inflammatory and metabolic pathways, including the NF-κB pathway (Shay, K. P. et al. *Biochim. Biophys. Acta* 2009, 1790, 1149-1160). Lipoic acid has been found to be useful in a number of chronic diseases that are associated with oxidative stress (for a review see Smith, A. R. et al *Curr. Med. Chem.* 2004, 11, p. 1135-46). Lipoic acid has now been evaluated in the clinic for the treatment of diabetes (Morcos, M. et al *Diabetes Res. Clin. Pract.* 2001, 52, p. 175-183) and diabetic neuropathy (Mijnhout, G. S. et al *Neth. J. Med.* 2010, 110, p. 158-162). Lipoic acid has also been found to be potentially useful in treating cardiovascular diseases (Ghibu, S. et al, *J. Cardiovasc. Pharmacol.* 2009, 54, p. 391-8), Alzheimer's disease (Maczurek, A. et al, *Adv. Drug Deliv. Rev.* 2008, 60, p. 1463-70) and multiple sclerosis (Yadav, V. *Multiple Sclerosis* 2005, 11, p. 159-65; Salinthone, S. et al, *Endocr. Metab. Immune Disord. Drug Targets* 2008, 8, p. 132-42). Lipoic acid can potentially be useful in treating or preventing hypertriglyceridemia and diabetic dyslipidemia. Recent data suggested that the triglyceride-lowering effect of lipoic acid is due in part to its ability to stimulate triglyceride clearance and down-regulate liver triglyceride secretion, most likely via inhibition of DGAT-2 (Moreau et al, *Archives of Biochemistry and Biophysics* 2009, 485, p. 63-71).

The ability to provide the effects of non-flushing niacin and omega-3 fatty acid in a synergistic way would provide a great benefit in treating the aforementioned diseases.

SUMMARY OF THE INVENTION

The invention is based in part on the discovery of fatty acid niacin conjugates and their demonstrated effects in achieving improved treatment that cannot be achieved by administering niacin or fatty acids alone or in combination. These novel conjugates are useful in the treatment or prevention of metabolic diseases including atherosclerosis, dyslipidemia, coronary heart disease, hypercholesterolemia, Type 2 diabetes, elevated cholesterol, metabolic syndrome and cardiovascular disease.

Accordingly in one aspect, a molecular conjugate is described which comprises a niacin covalently linked to a fatty acid, wherein the fatty acid is selected from the group consisting of omega-3 fatty acids and fatty acids that are metabolized in vivo to omega-3 fatty acids, the conjugate comprises at least one amide, and the conjugate is capable of hydrolysis to produce free niacin and free fatty acid.

In another aspect, a molecular conjugate is described which comprises a niacin covalently linked to a fatty acid, wherein the fatty acid is selected from the group consisting of omega-3 fatty acids and fatty acids that are metabolized in vivo to omega-3 fatty acids, wherein the niacin is not linked to the fatty acid through —OCH2O—, and the conjugate is capable of hydrolysis to produce free niacin and free fatty acid.

In another aspect, compounds of the Formula I are described:

Formula I

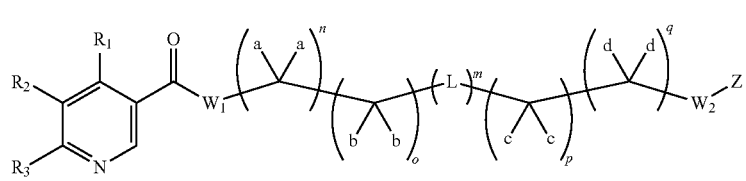

and pharmaceutically acceptable salts, hydrates, solvates, prodrugs, enantiomers and stereoisomers thereof;

wherein, $R_1$, $R_2$, and $R_3$ are each independently selected from the group consisting of —H, -D, —Cl, —F, —CN, —$NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —C(O)H, —C(O)$C_1$-$C_3$ alkyl, —C(O)O$C_1$-$C_3$ alkyl, —C(O)$NH_2$, —C(O)NH($C_1$-$C_3$ alkyl), —C(O)N($C_1$-$C_3$ alkyl)$_2$, —$C_1$-$C_3$ alkyl, —O—$C_1$-$C_3$ alkyl, —S(O)$C_1$-$C_3$ alkyl and —S(O)$_2$$C_1$-$C_3$ alkyl;

$W_1$ and $W_2$ are each independently null, O, S, NH, NR, or $W_1$ and $W_2$ can be taken together can form an imidazolidine or piperazine group, with the proviso that $W_1$ and $W_2$ can not be O simultaneously;

each a, b, c, and d is independently —H, -D, —$CH_3$, —$OCH_3$, —$OCH_2CH_3$, —C(O)OR, or —O—Z, or benzyl, or two of a, b, c, and d can be taken together, along with the single carbon to which they are bound, to form a cycloalkyl or heterocycle;

each n, o, p, and q is independently 0 or 1;

each L is independently —O—, —S—, —S(O)—, —S(O)$_2$, —S—S—,

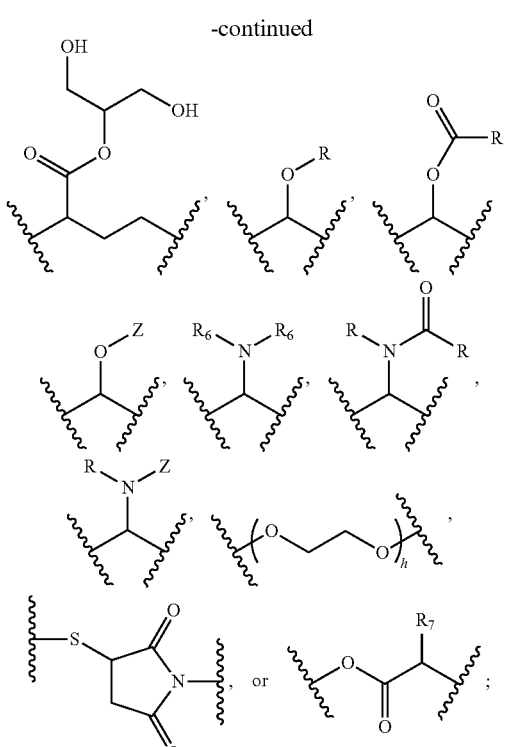

wherein the representation of L is not limited directionally left to right as depicted, rather either the left side or the right side of L can be bound to the $W_1$ side of the compound of Formula I;

each g is independently 2, 3 or 4;

each h is independently 1, 2, 3 or 4;

m is 0, 1, 2, or 3;

each $R_6$ is independently H or $C_1$-$C_6$ alkyl, or both $R_6$ groups, when taken together with the nitrogen to which they are attached, form a heterocycle;

each $R_7$ is independently e, H, or straight or branched $C_1$-$C_{10}$ alkyl which can be optionally substituted with OH, $NH_2$, $CO_2R$, $CONH_2$, phenyl, $C_6H_4OH$, imidazole or arginine;

each e is independently H or any one of the side chains of the naturally occurring amino acids;

each Z is independently —H, or

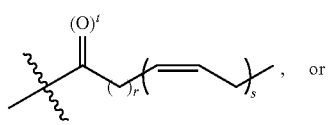

, or

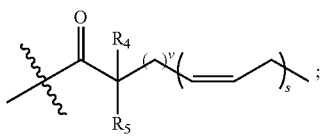

with the proviso that there is at least one

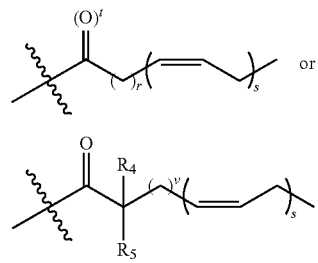

in the compound;

each r is independently 2, 3, or 7;

each s is independently 3, 5, or 6;

each t is independently 0 or 1;

each v is independently 1, 2, or 6;

$R_4$ and $R_5$ are each independently —H, -D, —$C_1$-$C_4$ alkyl, -halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, —$NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl; and each R is independently —H, —C(O)—$C_1$-$C_3$ alkyl, or straight or branched $C_1$-$C_4$ alkyl optionally substituted with OR, $NR_2$, or halogen;

provided that when m, n, o, p, and q are each 0, $W_1$ and $W_2$ are each null, and Z is

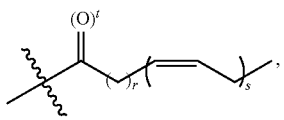

then t must be 0; and when each of m, n, o, p, and q is 0, and $W_1$ and $W_2$ are each null, then Z must not be

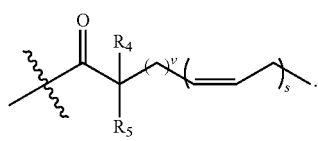

In another aspect, compounds of the Formula II are described:

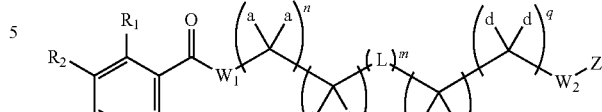

and pharmaceutically acceptable salts, hydrates, solvates, prodrugs, enantiomers and stereoisomers thereof;

wherein, $R_1$, $R_2$, and $R_3$ are each independently selected from the group consisting of —H, -D, —Cl, —F, —CN, —$NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —C(O)H, —C(O)$C_1$-$C_3$ alkyl, —C(O)O$C_1$-$C_3$ alkyl, —C(O)$NH_2$, —C(O)NH($C_1$-$C_3$ alkyl), —C(O)N($C_1$-$C_3$ alkyl)$_2$, —$C_1$-$C_3$ alkyl, —O—$C_1$-$C_3$ alkyl, —S(O)$C_1$-$C_3$ alkyl and —S(O)$_2$$C_1$-$C_3$ alkyl;

$W_1$ and $W_2$ are each independently selected from null, O, S, NH, and NR;

each a, b, c, and d is independently —H, -D, Halogen, —$CH_3$, —$OCH_3$, —$OCF_3$, —$OCH_2CH_3$, —C(O)OR, or —O—Z, or benzyl, or two of a, b, c, and d can be taken together, along with the single carbon to which they are bound, to form a cycloalkyl or heterocycle;

each n, o, p, and q is independently 0 or 1;

each L is independently —O—, —S—, —S(O)—, —S(O)$_2$—, —S—S—,

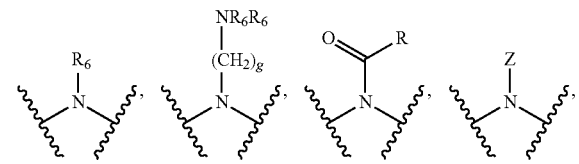

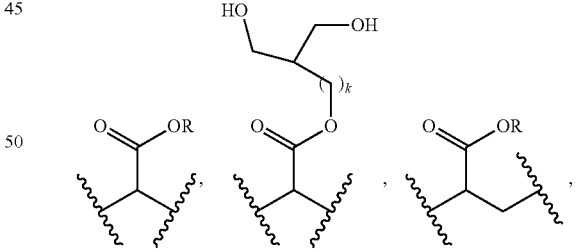

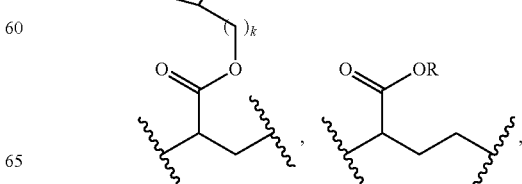
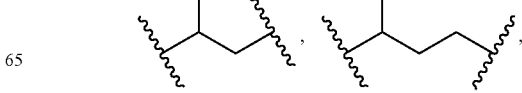

-continued

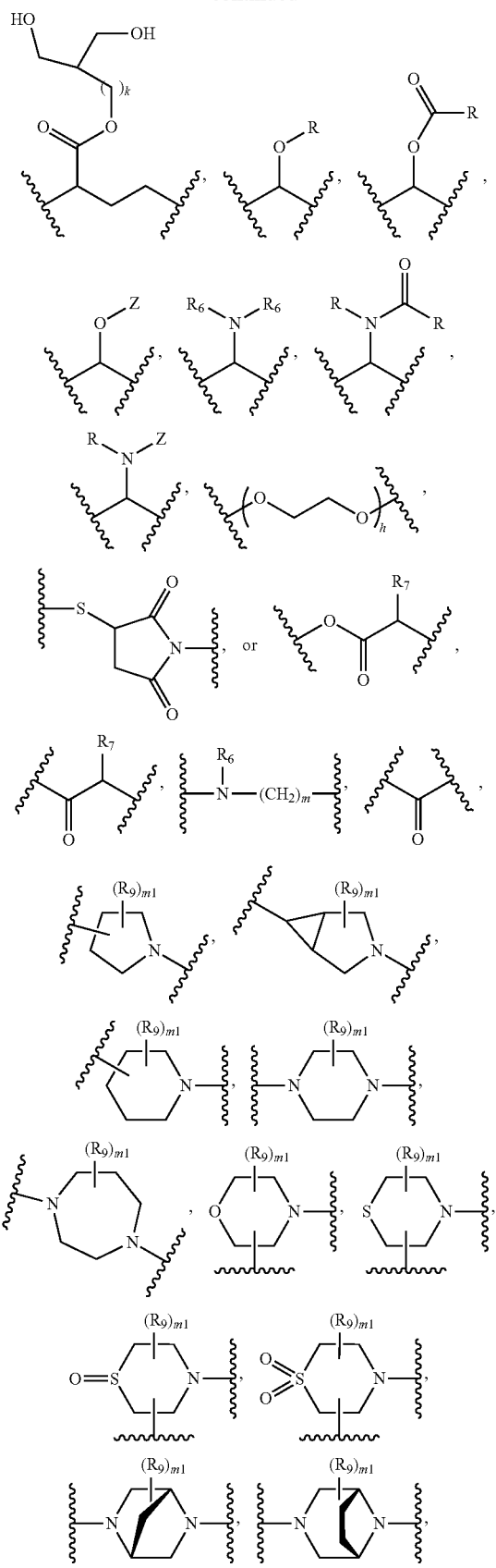

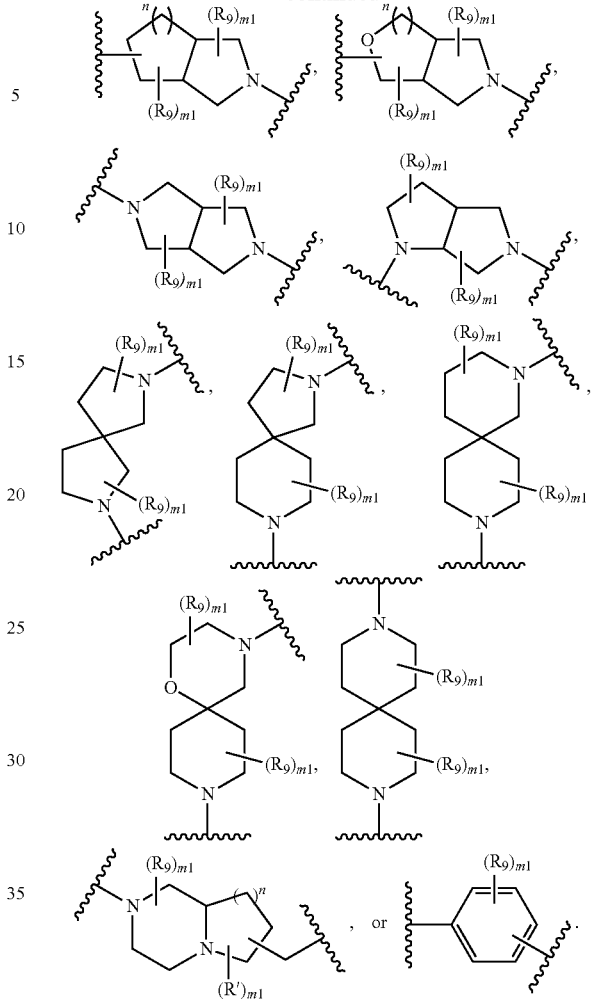

wherein the representation of L is not limited directionally left to right as depicted, rather either the left side or the right side of L can be bound to the $W_1$ side of the compound of Formula I;

each g is independently 2, 3 or 4;

each h is independently 1, 2, 3 or 4;

each m is independently 0, 1, 2, or 3; if m is more than 1, then L can be the same or different;

each m1 is independently 0, 1, 2, or 3;

k is 0, 1, 2, or 3;

each $R_6$ is independently H or $C_1$-$C_6$ alkyl, or both $R_6$ groups, when taken together with the nitrogen to which they are attached, form a heterocycle;

each $R_7$ is independently e, H, or straight or branched $C_1$-$C_{10}$ alkyl which can be optionally substituted with OH, $NH_2$, $CO_2R$, $CONH_2$, phenyl, $C_6H_4OH$, imidazole or arginine;

each e is independently H or any one of the side chains of the naturally occurring amino acids;

each $R_9$ is independently —H, -D, $C_1$-$C_4$ alkyl, halogen, cyano, oxo, thiooxo, —OH, $C(O)C_1$-$C_4$ alkyl, O-aryl, O-benzyl, $OC(O)C_1$-$C_4$ alkyl, $C_1$-$C_3$ alkene, $C_1$-$C_3$ alkyne, $C(O)C_1$-$C_4$ alkyl, $NH_2$, $NH(C_1$-$C_3$ alkyl), $N(C_1$-$C_3$ alkyl)$_2$, $NH(C(O)C_1$-$C_3$ alkyl), $N(C(O)C_1$-$C_3$ alkyl)$_2$, SH, $S(C_1$-$C_3$ alkyl), $S(O)C_1$-$C_3$ alkyl, $S(O)_2C_1$-$C_3$ alkyl;

each Z is independently —H, or

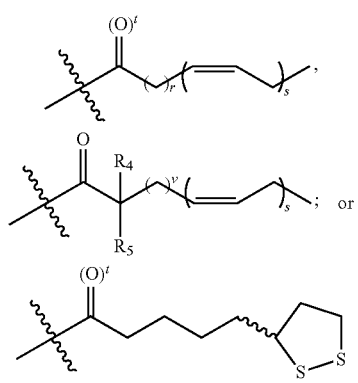

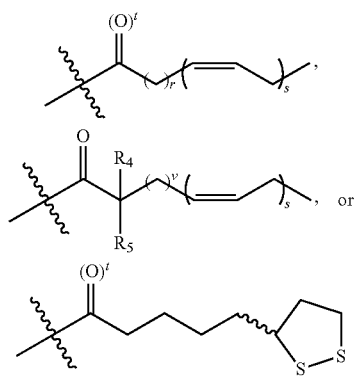

with the proviso that there is at least one in the compound;
each r is independently 2, 3, or 7;
each s is independently 3, 5, or 6;
each t is independently 0 or 1;
each v is independently 1, 2, or 6;
$R_4$ and $R_5$ are each independently —H, -D, —$C_1$-$C_4$ alkyl, -halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, —$NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl; and
each R is independently —H, —C(O)—$C_1$-$C_3$ alkyl, or straight or branched $C_1$-$C_4$ alkyl optionally substituted with OR, $NR_2$, or halogen;
provided that
when m, n, o, p, and q are each 0, $W_1$ and $W_2$ are each null, and Z is

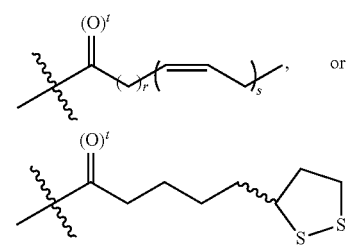

then t must be 0; and
when each of m, n, o, p, and q is 0, and $W_1$ and $W_2$ are each null, then Z must not be

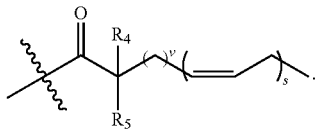

In Formula I and II, any one or more of H may be substituted with a deuterium. It is also understood in Formula I and II that a methyl substituent can be substituted with a $C_1$-$C_6$ alkyl.

Also described are pharmaceutical formulations comprising at least one fatty acid niacin derivative.

Also described herein are methods of treating a disease susceptible to treatment with a fatty acid niacin derivative in a patient in need thereof by administering to the patient an effective amount of a fatty acid niacin derivative.

Also described herein are methods of treating metabolic diseases by administering to a patient in need thereof an effective amount of a fatty acid niacin derivative.

The invention also includes pharmaceutical compositions that comprise an effective amount of a fatty acid niacin derivative and a pharmaceutically acceptable carrier. The compositions are useful for treating or preventing a metabolic disease. The invention includes a fatty acid niacin derivative provided as a pharmaceutically acceptable prodrug, hydrate, salt, enantiomer, stereoisomer, or mixtures thereof.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

DETAILED DESCRIPTION OF THE INVENTION

Figure 1:
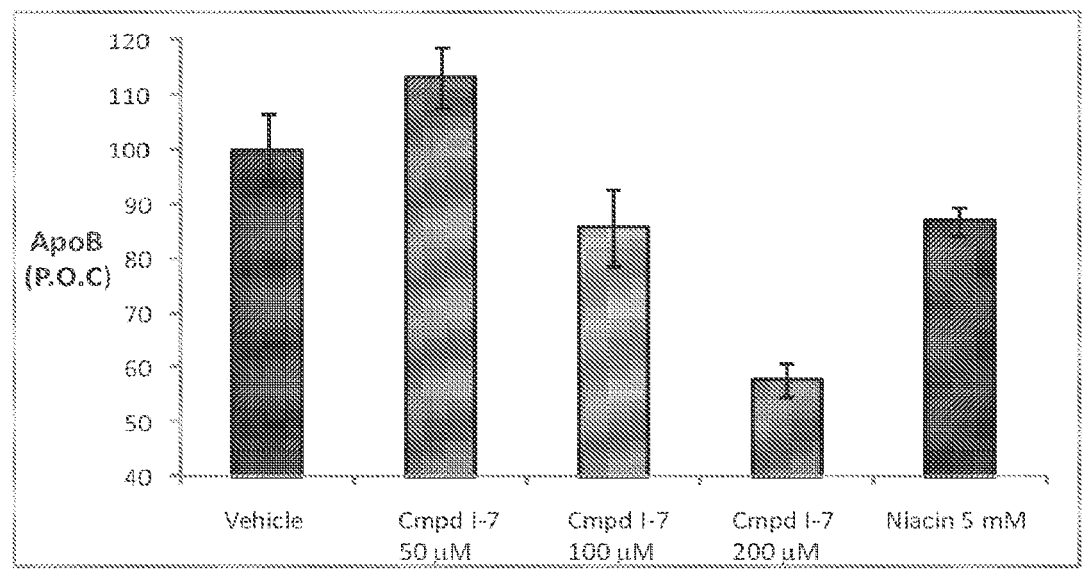
FIG. 1 is a depiction of the effect of compound I-7 on ApoB secretion in HepG2 cells.

Metabolic diseases are a wide variety of medical disorders that interfere with a subject's metabolism. Metabolism is the process a subject's body uses to transform food into energy. Metabolism in a subject with a metabolic disease is disrupted in some way. The fatty acid niacin derivatives possess the ability to treat or prevent metabolic diseases.

Accordingly in one aspect, a molecular conjugate is described which comprises a niacin covalently linked to a fatty acid, wherein the fatty acid is selected from the group consisting of omega-3 fatty acids and fatty acids that are metabolized in vivo to omega-3 fatty acids, the conjugate comprises at least one amide, and the conjugate is capable of hydrolysis to produce free niacin and free fatty acid.

In another aspect, a molecular conjugate is described which comprises a niacin covalently linked to a fatty acid, wherein the fatty acid is selected from the group consisting of omega-3 fatty acids and fatty acids that are metabolized in vivo to omega-3 fatty acids, wherein the niacin is not linked to the fatty acid through —OCH2O—, and the conjugate is capable of hydrolysis to produce free niacin and free fatty acid.

DEFINITIONS

The following definitions are used in connection with the fatty acid niacin derivatives:

The term "fatty acid niacin derivatives" includes any and all possible isomers, stereoisomers, enantiomers, diastereomers, tautomers, pharmaceutically acceptable salts, hydrates, solvates, and prodrugs of the fatty acid niacin derivatives described herein.

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

Unless otherwise specifically defined, the term "aryl" refers to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. The substituents can themselves be optionally substituted.

"$C_1$-$C_3$ alkyl" refers to a straight or branched chain saturated hydrocarbon containing 1-3 carbon atoms. Examples of a $C_1$-$C_3$ alkyl group include, but are not limited to, methyl, ethyl, propyl and isopropyl.

"$C_1$-$C_4$ alkyl" refers to a straight or branched chain saturated hydrocarbon containing 1-4 carbon atoms. Examples of a $C_1$-$C_4$ alkyl group include, but are not limited to, methyl, ethyl, propyl, butyl, isopropyl, isobutyl, sec-butyl and tert-butyl.

"$C_1$-$C_5$ alkyl" refers to a straight or branched chain saturated hydrocarbon containing 1-5 carbon atoms. Examples of a $C_1$-$C_5$ alkyl group include, but are not limited to, methyl, ethyl, propyl, butyl, pentyl, isopropyl, isobutyl, sec-butyl and tert-butyl, isopentyl and neopentyl.

"$C_1$-$C_6$ alkyl" refers to a straight or branched chain saturated hydrocarbon containing 1-6 carbon atoms. Examples of a $C_1$-$C_6$ alkyl group include, but are not limited to, methyl, ethyl, propyl, butyl, pentyl, hexyl, isopropyl, isobutyl, sec-butyl, tert-butyl, isopentyl, and neopentyl.

The term "cycloalkyl" refers to a cyclic hydrocarbon containing 3-6 carbon atoms. Examples of a cycloalkyl group include, but are not limited to, cyclopropyl, cyclobutyl, cyclopentyl and cyclohexyl.

It is understood that any of the substitutable hydrogens on an alkyl and cycloalkyl can be substituted with halogen, $C_1$-$C_3$ alkyl, hydroxyl, alkoxy and cyano groups.

The term "heterocycle" as used herein refers to an optionally substituted cyclic hydrocarbon containing 3-6 atoms wherein at least one of the atoms is an O, N, or S. Examples of heterocycles include, but are not limited to, aziridine, oxirane, thiirane, azetidine, oxetane, thietane, pyrrolidine, tetrahydrofuran, tetrahydrothiophene, piperidine, tetrahydropyran, tetrahydrofuran, thiane, imidazolidine, oxazolidine, thiazolidine, dioxolane, dithiolane, piperazine, oxazine, dithiane, and dioxane. Possible substituents that may optionally be attached to any carbon or nitrogen of the heterocycle include halogen, OH, OR, NHR, and $NR_2$, wherein the R can be the same or different when multiple Rs are present in the same heterocycle.

The term "any one of the side chains of the naturally occurring amino acids" as used herein means a side chain of any one of the following amino acids: Isoleucine, Alanine, Leucine, Asparagine, Lysine, Aspartate, Methionine, Cysteine, Phenylalanine, Glutamate, Threonine, Glutamine, Tryptophan, Glycine, Valine, Proline, Arginine, Serine, Histidine, and Tyrosine.

The term "fatty acid" as used herein means an omega-3 fatty acid and fatty acids that are metabolized in vivo to omega-3 fatty acids. Non-limiting examples of fatty acids are all-cis-7,10,13-hexadecatrienoic acid, α-linolenic acid (ALA or all-cis-9,12,15-octadecatrienoic acid), stearidonic acid (STD or all-cis-6,9,12,15-octadecatetraenoic acid), eicosatrienoic acid (ETE or all-cis-11,14,17-eicosatrienoic acid), eicosatetraenoic acid (ETA or all-cis-8,11,14,17-eicosatetraenoic acid), eicosapentaenoic acid (EPA or all-cis-5,8,11,14,17-eicosapentaenoic acid), docosapentaenoic acid (DPA, clupanodonic acid or all-cis-7,10,13,16,19-docosapentaenoic acid), docosahexaenoic acid (DHA or all-cis-4,7,10,13,16,19-docosahexaenoic acid), tetracosapentaenoic acid (all-cis-9,12,15,18,21-docosahexaenoic acid), or tetracosahexaenoic acid (nisinic acid or all-cis-6,9,12,15,18,21-tetracosenoic acid).

The term "niacin" as used herein means the molecule known as niacin and any derivative thereof.

A "subject" is a mammal, e.g., a human, mouse, rat, guinea pig, dog, cat, horse, cow, pig, or non-human primate, such as a monkey, chimpanzee, baboon or rhesus, and the terms "subject" and "patient" are used interchangeably herein.

The invention also includes pharmaceutical compositions comprising an effective amount of a fatty acid niacin derivative and a pharmaceutically acceptable carrier. The invention includes a fatty acid niacin derivative provided as a pharmaceutically acceptable prodrug, hydrate, salt, such as a pharmaceutically acceptable salt, enantiomers, stereoisomers, or mixtures thereof.

Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

The term "metabolic disease" as used herein refers to disorders, diseases and syndromes involving dyslipidemia, and the terms metabolic disorder, metabolic disease, and metabolic syndrome are used interchangeably herein.

An "effective amount" when used in connection with a fatty acid niacin derivative is an amount effective for treating or preventing a metabolic disease.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body.

The term "treating", with regard to a subject, refers to improving at least one symptom of the subject's disorder. Treating can be curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a compound or pharmaceutically acceptable salt of the compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a fatty acid niacin derivative.

The following abbreviations are used herein and have the indicated definitions: Boc and BOC are tert-butoxycarbonyl, $Boc_2O$ is di-tert-butyl dicarbonate, BSA is bovine serum albumin, CDI is 1,1'-carbonyldiimidazole, DCC is N,N'-dicyclohexylcarbodiimide, DIEA is N,N-diisopropylethylamine, DMAP is 4-dimethylaminopyridine, DMEM is Dulbecco's Modified Eagle Medium, DMF is N,N-dimethylformamide, DOSS is sodium dioctyl sulfosuccinate, EDC and EDCI are 1-ethyl-3-(3-dimethylaminopropyl)carbodiimide hydrochloride, ELISA is enzyme-linked immunosorbent assay, EtOAc is ethyl acetate, FBS is fetal bovine serum, h is hour, HATU is 2-(7-aza-1H-benzotriazole-1-yl)-1,1,3,3-tetramethyluronium hexafluorophosphate, HIV is human immunodeficiency virus, HPMC is hydroxypropyl methylcellulose, oxone is potassium peroxymonosulfate, Pd/C is palladium on carbon, TFA is trifluoroacetic acid, TGPS is tocopherol propylene glycol succinate, and THF is tetrahydrofuran.

Compounds

Accordingly in one aspect, a molecular conjugate is described which comprises a niacin covalently linked to a fatty acid, wherein the fatty acid is selected from the group consisting of omega-3 fatty acids and fatty acids that are metabolized in vivo to omega-3 fatty acids, wherein the niacin is not linked to the fatty acid through —$OCH_2O$—, and the conjugate is capable of hydrolysis to produce free niacin and free fatty acid.

In some embodiments, the fatty acid is selected from the group consisting of all-cis-7,10,13-hexadecatrienoic acid, α-linolenic acid, stearidonic acid, eicosatrienoic acid, eicosatetraenoic acid, eicosapentaenoic acid (EPA), docosapentaenoic acid, docosahexaenoic acid (DHA), tetracosapentaenoic acid and tetracosahexaenoic acid. In other embodiments, the fatty acid is selected from eicosapentaenoic acid and docosahexaenoic acid. In some embodiments, the hydrolysis is enzymatic.

In another aspect, the present invention provides fatty acid niacin derivatives according to Formula I:

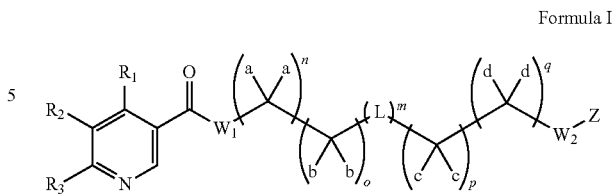

Formula I and pharmaceutically acceptable salts, hydrates, solvates, prodrugs, enantiomers, and stereoisomers thereof;

wherein $R_1$, $R_2$, $R_3$, $R_4$, $R_5$, $R_6$, $R_7$, R, $W_1$, $W_2$, L, a, c, b, d, e, g, h, m, n, o, p, q, Z, r, s, t, and v are as defined above for Formula I, with the proviso that there is at least one

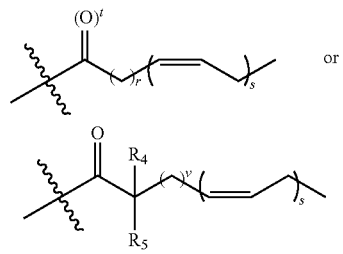

in the compound.

In another aspect, the present invention provides fatty acid niacin derivatives according to Formula II:

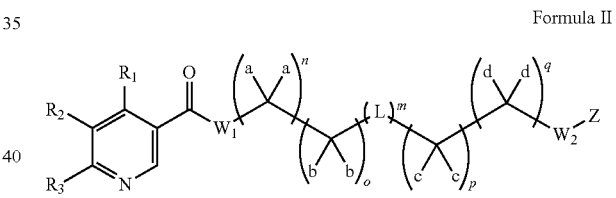

Formula II and pharmaceutically acceptable salts, hydrates, solvates, prodrugs, enantiomers, and stereoisomers thereof;

wherein $R_1$, $R_2$, $R_3$, $R_4$, $R_5$, $R_6$, $R_7$, R, $W_1$, $W_2$, L, a, c, b, d, e, g, h, m, n, o, p, q, Z, r, s, t, and v are as defined above for Formula II, with the proviso that there is at least one

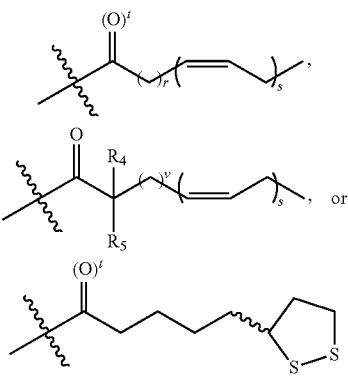

in the compound.

The following embodiments describe different embodiments of Formula I and Formula II:

In some embodiments, $R_3$ is Cl, F, or CN.

In some embodiments, $R_3$ is —CH$_3$ or —CH$_2$CH$_3$.

In some embodiments, $W_1$ is NH.

In some embodiments, $W_2$ is NH.

In some embodiments, $W_1$ is O.

In some embodiments, $W_2$ is O.

In some embodiments, $W_1$ is O and $W_2$ is NH.

In some embodiments, $W_1$ is NH and $W_2$ is O.

In some embodiments, a and c are each independently H, or CH$_3$.

In some embodiments, a and c are each independently H, or F.

In some embodiments, m is 0.

In other embodiments, m is 1.

In some embodiments, L is —S, or —S—S—.

In some embodiments, L is —O—,

In some embodiments, L is

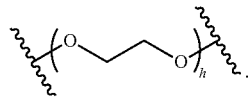

In some embodiments, L is

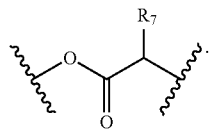

In some embodiments, L is

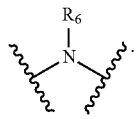

In some embodiments, L is

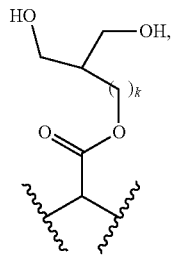 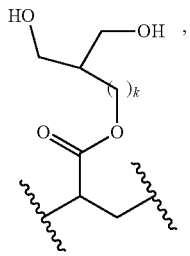 or

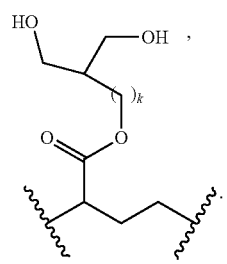

In some embodiments, L is

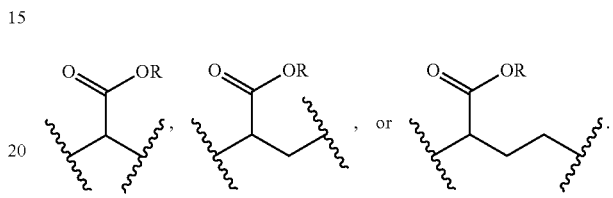

In some embodiments, L is

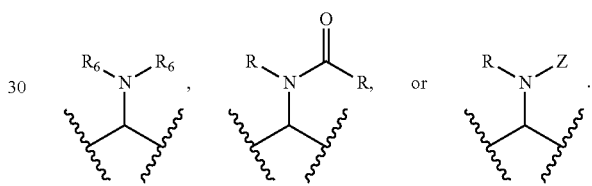

In some embodiments, L is

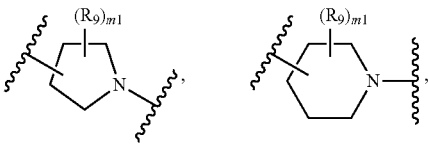

In some embodiments, L is

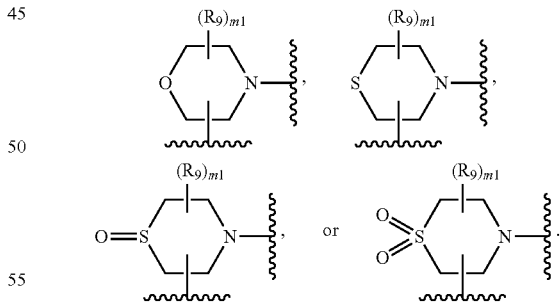

In some embodiments, L is

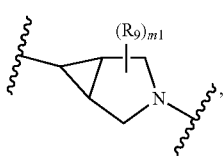 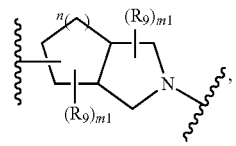

-continued

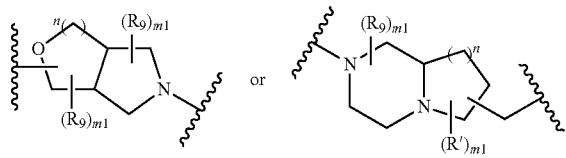

In some embodiments, L is

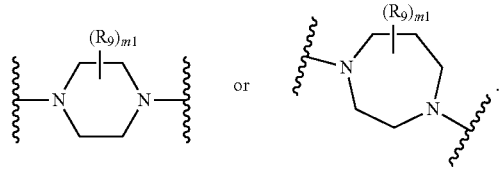

In some embodiments, L is

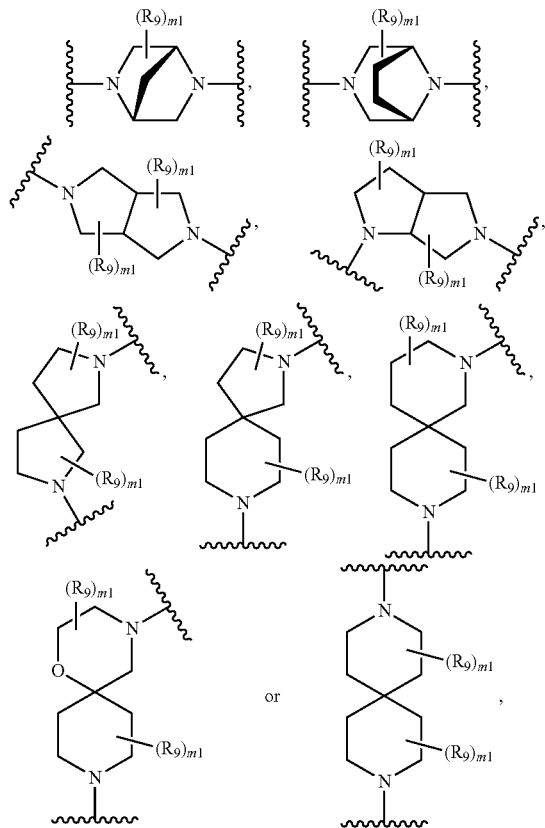

In some embodiments, one b is O—Z, Z is

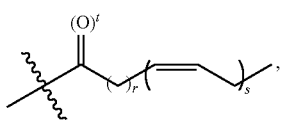

and t is 1.
In some embodiments, one d is C(O)OR.
In some embodiments n, o, p, and q are each 1.

In some embodiments, two of n, o, p, and q are each 1.
In other embodiments, three of n, o, p, and q are each 1.
In some embodiments, one Z is

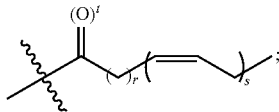

and r is 2.
In some embodiments, one Z is

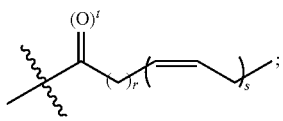

and r is 3.
In some embodiments, one Z is

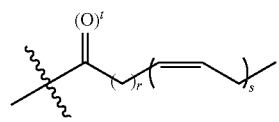

and r is 7.
In other embodiments, one Z is

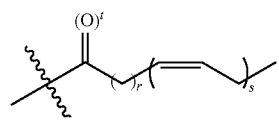

and s is 3.
In some embodiments, one Z is

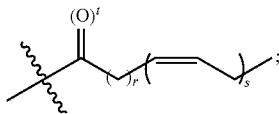

and s is 5.
In some embodiments, one Z is

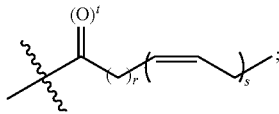

and s is 6.

In some embodiments, one Z is

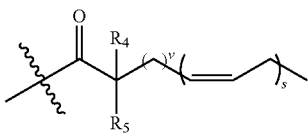

and v is 1.

In other embodiments, one Z is

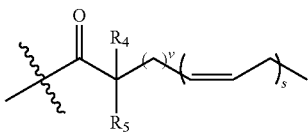

and v is 2.

In some embodiments, one Z is

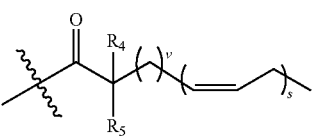

and v is 6.

In some embodiments, one Z is

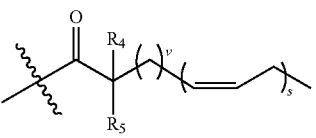

and s is 3.

In some embodiments, one Z is

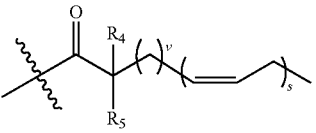

and s is 5.

In other embodiments, one Z is

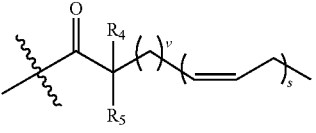

and s is 6.

In some embodiments, Z is

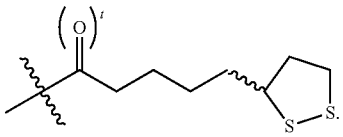

In some embodiments, t is 1.

In some embodiments, r is 2, s is 6, $W_1$ and $W_2$ are each O, m is 0, and one of n, o, p, and q is 1.

In some embodiments, r is 3, s is 5, $W_1$ and $W_2$ are each O, m is 0, and one of n, o, p, and q is 1.

In some embodiments, r is 2, s is 6, one of $W_1$ and $W_2$ is NH, m is 0, and one of n, o, p, and q are 1.

In some embodiments, r is 3, s is 5, one of $W_1$ and $W_2$ is NH, m is 0, and one of n, o, p, and q are 1.

In some embodiments, r is 2, s is 6, $W_1$ and $W_2$ are each O, m is 0, and two of n, o, p, and q are 1.

In some embodiments, r is 3, s is 5, $W_1$ and $W_2$ are each O, m is 0, and two of n, o, p, and q are 1.

In some embodiments, r is 2, s is 6, one of $W_1$ and $W_2$ is NH, m is 0, and two of n, o, p, and q are 1.

In some embodiments, r is 3, s is 5, one of $W_1$ and $W_2$ is NH, m is 0, and two of n, o, p, and q are 1.

In some embodiments, r is 2, s is 6, $W_1$ and $W_2$ are each O, m is 0, two of n, o, p, and q are 1, and two of n, o, p, and q are 0.

In some embodiments, r is 3, s is 5, $W_1$ and $W_2$ are each O, m is 0, two of n, o, p, and q are 1, and two of n, o, p, and q are 0.

In some embodiments, r is 2, s is 6, one of $W_1$ and $W_2$ is NH, m is 0, two of n, o, p, and q are 1, and two of n, o, p, and q are 0.

In some embodiments, r is 3, s is 5, one of $W_1$ and $W_2$ is NH, m is 0, two of n, o, p, and q are 1, and two of n, o, p, and q are 0.

In some embodiments, r is 2, s is 6, $W_1$ and $W_2$ are each O, m is 0, and three of n, o, p, and q are 1.

In some embodiments, r is 3, s is 5, $W_1$ and $W_2$ are each O, m is 0, and three of n, o, p, and q are 1.

In some embodiments, r is 2, s is 6, one of $W_1$ and $W_2$ is NH, m is 0, and three of n, o, p, and q are 1.

In some embodiments, r is 3, s is 5, one of $W_1$ and $W_2$ is NH, m is 0, and three of n, o, p, and q are 1.

In some embodiments, r is 2, s is 6, one of $W_1$ and $W_2$ is NH, m is 1, n, o, p, and q are each 1, and L is O.

In some embodiments, r is 2, s is 6, one of $W_1$ and $W_2$ is NH, m is 1, n, o, p, and q are each 1, and L is —S—S—.

In some embodiments, r is 2, s is 6, one of $W_1$ and $W_2$ is NH, m is 1, n and o are each 0, p and q are each 1, and L is

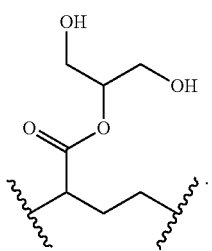 [SMILES: *CCC(*)C(=O)OC(CO)CO]

In some embodiments, r is 2, s is 6, one of $W_1$ and $W_2$ is NH, m is 1, n, o, p, and q are each 0, and L is

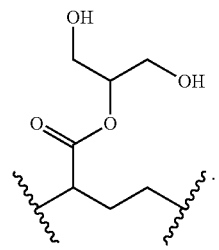 [SMILES: *CCC(*)C(=O)OC(CO)CO]

In some embodiments, r is 2, s is 6, one of $W_1$ and $W_2$ is NH, m, n, and o are each 0, and p and q are each 1.

In some embodiments, r is 2, s is 6, one of $W_1$ and $W_2$ is NH, m is 1, n and o are each 0, p and q are each 1, and L is

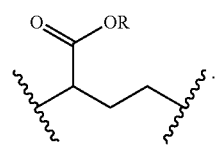

In some embodiments, r is 2, s is 6, one of $W_1$ and $W_2$ is NH, m is 1, n and o are each 1, p and q are each 0, and L is

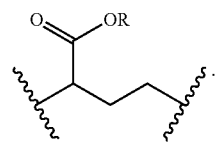

In some embodiments, r is 2, s is 6, m is 1, n and o are each 0, p and q are each 1, and L is

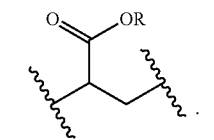

In some embodiments, r is 2, s is 6, m is 1, n and o are each 1, p and q are each 0, and L is

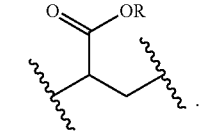

In some embodiments, r is 2, s is 6, $W_1$ and $W_2$ are each NH, m is 1, n, o, p, and q are each 1, and L is

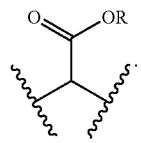

In some embodiments, r is 2, s is 6, one of $W_1$ and $W_2$ is NH, m is 1, n, o, p, and q are each 1, and L is $NR_6$.

In some embodiments, r is 2, s is 6, one of $W_1$ and $W_2$ is NH, m, n, and o are each 0, and p and q are each 1, and one c is —$CH_3$ and the other c is —$CH_3$.

In some embodiments, r is 2, s is 6, one of $W_1$ and $W_2$ is NH, m is 1, n and o are each 1, p and q are each 0, and L is

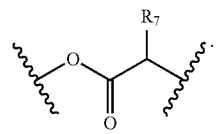

In some embodiments, r is 3, s is 5, and L is —S—S—.
In some embodiments, r is 3, s is 5, and L is —O—.
In some embodiments, r is 3, s is 5, and L is

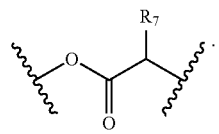

In some embodiments, r is 3, s is 5, and L is

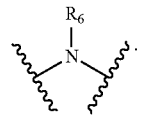

In some embodiments, r is 3, s is 5, and L is

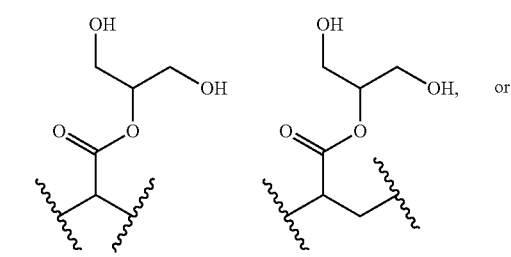

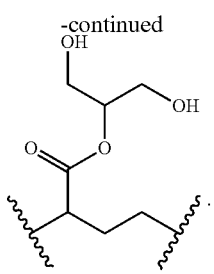

In some embodiments, r is 3, s is 5, and L is

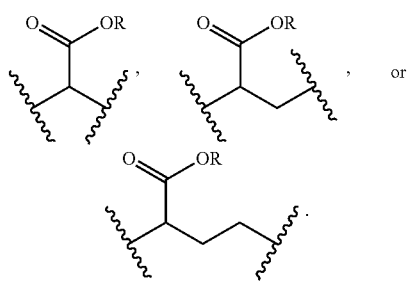

In some embodiments, r is 3, s is 5, and n, o, p, and q are each 1.

In some embodiments, r is 3, s is 5, and two of n, o, p, and q are each 1.

In some embodiments, r is 3, s is 5, m is 1, n, o, p, and q are each 1, and L is O.

In some embodiments, r is 3, s is 5, m is 1, n, o, p, and q are each 1, and L is —S—S—.

In some embodiments, r is 3, s is 5, m is 1, n and o are each 0, p and q are each 1, and L is

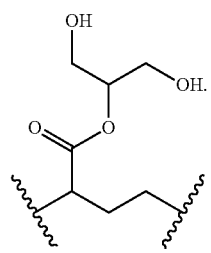 [SMILES: *CCC(*)C(=O)OC(CO)CO]

In some embodiments, r is 3, s is 5, m is 1, n, o, p, and q are each 0, and L is

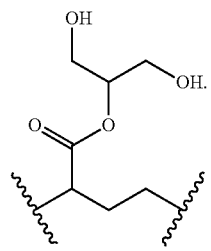 [SMILES: *CCC(*)C(=O)OC(CO)CO]

In some embodiments, r is 3, s is 5, m, n, and o are each 0, and p and q are each 1.

In some embodiments, r is 3, s is 5, m is 1, n and o are each 1, p and q are each 0, and L is

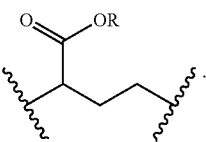

In some embodiments, r is 3, s is 5, m is 1, n and o are each 0, p and q are each 1, and L is

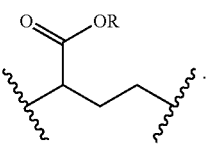

In some embodiments, r is 3, s is 5, m is 1, n and o are each 0, p and q are each 1, and L is

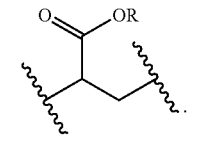

In some embodiments, r is 3, s is 5, m is 1, n and o are each 1, p and q are each 0, and L is

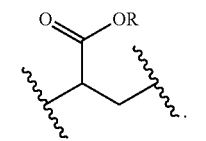

In some embodiments, r is 3, s is 5, m is 1, n, o, p, and q are each 1, and L is $NR_6$.

In some embodiments, r is 3, s is 5, m, n, and o are each 0, and p and q are each 1, and one c is —$CH_3$ and the other c is —$CH_3$.

In some embodiments, r is 3, s is 5, m is 1, n and o are each 1, p and q are each 0, and

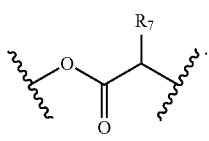

In Formula I and Formula II, any one or more of H may be substituted for a deuterium. It is also understood in Formula I and Formula II that a methyl substituent have as a substituent a $C_1$-$C_6$ alkyl.

In other illustrative embodiments, compounds of Formula I are as set forth below:

N-(2-(2-(4Z,7Z,10Z,13Z,16Z,19Z)-docosa-4,7,10,13,16,19-hexaenamidoethoxy)ethyl)nicotinamide (I-1);

N-(2-((2-(4Z,7Z,10Z,13Z,16Z,19Z)-docosa-4,7,10,13,16, 19-hexaenamidoethyl)(methyl)amino)ethyl)nicotinamide (I-2);

N-(2-(2-(2-(4Z,7Z,10Z,13Z,16Z,19Z)-docosa-4,7,10,13,16,
19-hexaenamidoethyl)disulfanyl)ethyl)nicotinamide
(I-3);
N-(2-(1-(2-(4Z,7Z,10Z,13Z,16Z,19Z)-docosa-4,7,10,13,16,
19-hexaenamidoethyl)-2,5-dioxopyrrolidin-3-ylthio)
ethyl)nicotinamide (I-4);
Methyl 3-(2-(4Z,7Z,10Z,13Z,16Z,19Z)-docosa-4,7,10,13,
16,19-hexaenamidoacetoxy)-2-(nicotinamido)butanoate
(I-5);
1,3-dihydroxypropan-2-yl 6-(4Z,7Z,10Z,13Z,16Z,19Z)-
docosa-4,7,10,13,16,19-hexaenamido-2-(nicotinamido)
hexanoate (I-6);
N-(2-(4Z,7Z,10Z,13Z,16Z,19Z)-docosa-4,7,10,13,16,19-
hexaenamidoethyl)nicotinamide (I-7);
N-(2-(5Z,8Z,11Z,14Z,17Z)-eicosa-5,8,11,14,17-pentaena-
midoethyl)nicotinamide (I-8);
(2S,3R)-methyl 3-((S)-2-((4Z,7Z,10Z,13Z,16Z,19Z)-
docosa-4,7,10,13,16,19-hexaenamido)propanoyloxy)-2-
(nicotinamido)butanoate (I-9);
(2S,3R)-methyl 3-((S)-2-((5Z,8Z,11Z,14Z,17Z)-icosa-5,8,
11,14,17-pentaenamido)propanoyloxy)-2-(nicotinamido)
butanoate (I-10);
(S)-methyl 6-((4Z,7Z,10Z,13Z,16Z,19Z)-docosa-4,7,10,13,
16,19-hexaenamido)-2-(nicotinamido)hexanoate (I-11);
(S)-6-((4Z,7Z,10Z,13Z,16Z,19Z)-docosa-4,7,10,13,16,19-
hexaenamido)-2-(nicotinamido)hexanoic acid (I-12);
(S)-methyl 2-((5Z,8Z,11Z,14Z,17Z)-eicosa-5,8,11,14,17-
pentaenamido)-6-(nicotinamido)hexanoate (I-13);
(S)-2-((5Z,8Z,11Z,14Z,17Z)-eicosa-5,8,11,14,17-pentaena-
mido)-6-(nicotinamido)hexanoic acid (I-14);
(S)-methyl 6-((5Z,8Z,11Z,14Z,17Z)-eicosa-5,8,11,14,17-
pentaenamido)-2-(nicotinamido)hexanoate (I-15);
(S)-6-((5Z,8Z,11Z,14Z,17Z)-eicosa-5,8,11,14,17-pentaena-
mido)-2-(nicotinamido)hexanoic acid (I-16);
(S)-2-((4Z,7Z,10Z,13Z,16Z,19Z)-docosa-4,7,10,13,16,19-
hexaenamido)-6-(nicotinamido)hexanoic acid (I-17);
(S)-5-((4Z,7Z,10Z,13Z,16Z,19Z)-docosa-4,7,10,13,16,19-
hexaenamido)-2-(nicotinamido)pentanoic acid (I-18);
(S)-2-((4Z,7Z,10Z,13Z,16Z,19Z)-docosa-4,7,10,13,16,19-
hexaenamido)-5-(nicotinamido)pentanoic acid (I-19);
4-(4Z,7Z,10Z,13Z,16Z,19Z)-docosa-4,7,10,13,16,19-
hexaenamido-2-(nicotinamido)butanoic acid (I-20);
2-(4Z,7Z,10Z,13Z,16Z,19Z)-docosa-4,7,10,13,16,19-
hexaenamido-4-(nicotinamido)butanoic acid (I-21);
3-(4Z,7Z,10Z,13Z,16Z,19Z)-docosa-4,7,10,13,16,19-
hexaenamido-2-(nicotinamido)propanoic acid (I-22);
2-(4Z,7Z,10Z,13Z,16Z,19Z)-docosa-4,7,10,13,16,19-
hexaenamido-3-(nicotinamido)propanoic acid (I-23);
2-(2-(4Z,7Z,10Z,13Z,16Z,19Z)-docosa-4,7,10,13,16,19-
hexaenamidoethyl)-4-(nicotinamido)butanoic acid (I-24);
(S)-1,3-dihydroxypropan-2-yl 2-((4Z,7Z,10Z,13Z,16Z,
19Z)-docosa-4,7,10,13,16,19-hexaenamido)-6-(nicotina-
mido)hexanoate (I-25);
(S)-1,3-dihydroxypropan-2-yl 5-((4Z,7Z,10Z,13Z,16Z,
19Z)-docosa-4,7,10,13,16,19-hexaenamido)-2-(nicotina-
mido)pentanoate (I-26);
(S)-1,3-dihydroxypropan-2-yl 2-((4Z,7Z,10Z,13Z,16Z,
19Z)-docosa-4,7,10,13,16,19-hexaenamido)-5-(nicotina-
mido)pentanoate (I-27);
1,3-dihydroxypropan-2-yl 4-(4Z,7Z,10Z,13Z,16Z,19Z)-
docosa-4,7,10,13,16,19-hexaenamido-2-(nicotinamido)
butanoate (I-28);
1,3-dihydroxypropan-2-yl 2-(4Z,7Z,10Z,13Z,16Z,19Z)-
docosa-4,7,10,13,16,19-hexaenamido-4-(nicotinamido)
butanoate (I-29);

1,3-dihydroxypropan-2-yl 3-(4Z,7Z,10Z,13Z,16Z,19Z)-
docosa-4,7,10,13,16,19-hexaenamido-2-(nicotinamido)
propanoate (I-30);
1,3-dihydroxypropan-2-yl 2-(4Z,7Z,10Z,13Z,16Z,19Z)-
docosa-4,7,10,13,16,19-hexaenamido-3-(nicotinamido)
propanoate (I-31);
1,3-dihydroxypropan-2-yl 2-(2-(4Z,7Z,10Z,13Z,16Z,19Z)-
docosa-4,7,10,13,16,19-hexaenamidoethyl)-4-(nicotina-
mido)butanoate (I-32);
N-(4-(4Z,7Z,10Z,13Z,16Z,19Z)-docosa-4,7,10,13,16,19-
hexaenamidobutyl)nicotinamide (I-33);
N-(3-(4Z,7Z,10Z,13Z,16Z,19Z)-docosa-4,7,10,13,16,19-
hexaenamidopropyl)nicotinamide (I-34);
N-(1-(4Z,7Z,10Z,13Z,16Z,19Z)-docosa-4,7,10,13,16,19-
hexaenamido-2-methylpropan-2-yl)nicotinamide (I-35);
N-(2-(4Z,7Z,10Z,13Z,16Z,19Z)-docosa-4,7,10,13,16,19-
hexaenamido-2-methylpropyl)nicotinamide (I-36);
N-(2-(2-(4Z,7Z,10Z,13Z,16Z,19Z)-docosa-4,7,10,13,16,19-
hexaenamidoethylamino)ethyl)nicotinamide (I-37);
N-(3-(2-(4Z,7Z,10Z,13Z,16Z,19Z)-docosa-4,7,10,13,16,19-
hexaenamidoethylamino)propyl)nicotinamide (I-38);
N-(2-(3-(4Z,7Z,10Z,13Z,16Z,19Z)-docosa-4,7,10,13,16,19-
hexaenamidopropylamino)ethyl)nicotinamide (I-39);
N-(2-((3-(4Z,7Z,10Z,13Z,16Z,19Z)-docosa-4,7,10,13,16,
19-hexaenamidopropyl)(ethyl)amino)ethyl)nicotinamide
(I-40);
N-(2-((2-(4Z,7Z,10Z,13Z,16Z,19Z)-docosa-4,7,10,13,16,
19-hexaenamidoethyl)(isobutyl)amino)ethyl)nicotina-
mide (I-41);
N-(2-(N-(2-(4Z,7Z,10Z,13Z,16Z,19Z)-docosa-4,7,10,13,
16,19-hexaenamidoethyl)acetamido)ethyl)nicotinamide
(I-42);
N-(2-((2-(4Z,7Z,10Z,13Z,16Z,19Z)-docosa-4,7,10,13,16,
19-hexaenamidoethyl)(2-morpholinoethyl)amino)ethyl)
nicotinamide (I-43);
N-(2-((2-(4Z,7Z,10Z,13Z,16Z,19Z)-docosa-4,7,10,13,16,
19-hexaenamidoethyl)(3-(piperazin-1-yl)propyl)amino)
ethyl)nicotinamide (I-44);
N-(3-(4Z,7Z,10Z,13Z,16Z,19Z)-docosa-4,7,10,13,16,19-
hexaenamido-2-oxopropyl)nicotinamide (I-45);
N-(3-(4Z,7Z,10Z,13Z,16Z,19Z)-docosa-4,7,10,13,16,19-
hexaenamido-2-morpholinopropyl)nicotinamide (I-46);
N-(3-(4Z,7Z,10Z,13Z,16Z,19Z)-docosa-4,7,10,13,16,19-
hexaenamido-2-(piperazin-1-yl)propyl)nicotinamide
(I-47);
N-(3-(4Z,7Z,10Z,13Z,16Z,19Z)-docosa-4,7,10,13,16,19-
hexaenamido-2-(4-methylpiperazin-1-yl)propyl)nicotina-
mide (I-48);
N-(5-(4Z,7Z,10Z,13Z,16Z,19Z)-docosa-4,7,10,13,16,19-
hexaenamido-3-hydroxypentyl)nicotinamide (I-49);
N-(5-(4Z,7Z,10Z,13Z,16Z,19Z)-docosa-4,7,10,13,16,19-
hexaenamido-3-morpholinopentyl)nicotinamide (I-50);
N-(5-(4Z,7Z,10Z,13Z,16Z,19Z)-docosa-4,7,10,13,16,19-
hexaenamido-3-(piperazin-1-yl)pentyl)nicotinamide
(I-51);
(S)—((R)-1-(nicotinamido)propan-2-yl) 2-((5Z,8Z,11Z,
14Z,17Z)-eicosa-5,8,11,14,17-pentaenamido)propanoate
(I-52);
(S)—((R)-1-(nicotinamido)propan-2-yl) 2-((5Z,8Z,11Z,
14Z,17Z)-eicosa-5,8,11,14,17-pentaenamido)-3-meth-
ylbutanoate (I-53);
N-(2-(2-(2-(4Z,7Z,10Z,13Z,16Z,19Z)-docosa-4,7,10,13,16,
19-hexaenamidoethoxy)ethoxy)ethyl)nicotinamide
(I-54);
N-(2-(2-(4Z,7Z,10Z,13Z,16Z,19Z)-docosa-4,7,10,13,16,19-
hexaenamidoethylthio)ethyl)nicotinamide (I-55);

(4Z,7Z,10Z,13Z,16Z,19Z)-1-(nicotinamido)propan-2-yl docosa-4,7,10,13,16,19-hexaenoate (I-56);
(4Z,7Z,10Z,13Z,16Z,19Z)-4-methoxy-3-(nicotinamido)-4-oxobutan-2-yl docosa-4,7,10,13,16,19-hexaenoate (I-57);
N-(2-(4Z,7Z,10Z,13Z,16Z,19Z)-docosa-4,7,10,13,16,19-hexaenamidoethyl)-6-methylnicotinamide (I-58);
N-(2-(5Z,8Z,11Z,14Z,17Z)-eicosa-5,8,11,14,17-pentaenamidoethyl)-6-methylnicotinamide (I-59);
N-(2-(4Z,7Z,10Z,13Z,16Z,19Z)-docosa-4,7,10,13,16,19-hexaenamidoethyl)-6-ethylnicotinamide (I-60);
6-ethyl-N-(2-(5Z,8Z,11Z,14Z,17Z)-eicosa-5,8,11,14,17-pentaenamidoethyl)nicotinamide (I-61);
6-chloro-N-(2-(4Z,7Z,10Z,13Z,16Z,19Z)-docosa-4,7,10,13,16,19-hexaenamidoethyl)nicotinamide (I-62);
6-chloro-N-(2-(5Z,8Z,11Z,14Z,17Z)-eicosa-5,8,11,14,17-pentaenamidoethyl)nicotinamide (I-63);
N-(2-(4Z,7Z,10Z,13Z,16Z,19Z)-docosa-4,7,10,13,16,19-hexaenamidoethyl)-6-fluoronicotinamide (I-64);
6-fluoro-N-(2-(5Z,8Z,11Z,14Z,17Z)-eicosa-5,8,11,14,17-pentaenamidoethyl)nicotinamide (I-65);
6-cyano-N-(2-(4Z,7Z,10Z,13Z,16Z,19Z)-docosa-4,7,10,13,16,19-hexaenamidoethyl)nicotinamide (I-66);
6-cyano-N-(2-(5Z,8Z,11Z,14Z,17Z)-eicosa-5,8,11,14,17-pentaenamidoethyl)nicotinamide (I-67);
(S)-6-((4Z,7Z,10Z,13Z,16Z,19Z)-docosa-4,7,10,13,16,19-hexaenamido)-2-(2-methylnicotinamido)hexanoic acid (I-68);
(S)-2-((4Z,7Z,10Z,13Z,16Z,19Z)-docosa-4,7,10,13,16,19-hexaenamido)-6-(2-methylnicotinamido)hexanoic acid (I-69);
(S)-6-((4Z,7Z,10Z,13Z,16Z,19Z)-docosa-4,7,10,13,16,19-hexaenamido)-2-(2-ethylnicotinamido)hexanoic acid (I-70);
(S)-2-((4Z,7Z,10Z,13Z,16Z,19Z)-docosa-4,7,10,13,16,19-hexaenamido)-6-(2-ethylnicotinamido)hexanoic acid (I-71);
(S)-2-(2-chloronicotinamido)-6-((4Z,7Z,10Z,13Z,16Z,19Z)-docosa-4,7,10,13,16,19-hexaenamido)hexanoic acid (I-72);
(S)-6-(2-chloronicotinamido)-2-((4Z,7Z,10Z,13Z,16Z,19Z)-docosa-4,7,10,13,16,19-hexaenamido)hexanoic acid (I-73);
(S)-6-((4Z,7Z,10Z,13Z,16Z,19Z)-docosa-4,7,10,13,16,19-hexaenamido)-2-(2-fluoronicotinamido)hexanoic acid (I-74);
(S)-2-((4Z,7Z,10Z,13Z,16Z,19Z)-docosa-4,7,10,13,16,19-hexaenamido)-6-(2-fluoronicotinamido)hexanoic acid (I-75);
(S)-2-(2-cyanonicotinamido)-6-((4Z,7Z,10Z,13Z,16Z,19Z)-docosa-4,7,10,13,16,19-hexaenamido)hexanoic acid (I-76);
(S)-6-(2-cyanonicotinamido)-2-((4Z,7Z,10Z,13Z,16Z,19Z)-docosa-4,7,10,13,16,19-hexaenamido)hexanoic acid (I-77);
N-(2-(2-(4Z,7Z,10Z,13Z,16Z,19Z)-docosa-4,7,10,13,16,19-hexaenamidoethoxy)ethyl)-6-methylnicotinamide (I-78);
N-(2-((2-(4Z,7Z,10Z,13Z,16,19-hexaenamidoethyl)(methyl)amino)ethyl)-6-methylnicotinamide (I-79);
N-(2-(2-(2-(4Z,7Z,10Z,13Z,16Z,19Z)-docosa-4,7,10,13,16,19-hexaenamidoethyl)disulfanyl)ethyl)-6-methylnicotinamide (I-80);
N-(2-(2-(4Z,7Z,10Z,13Z,16Z,19Z)-docosa-4,7,10,13,16,19-hexaenamidoethoxy)ethyl)-6-ethylnicotinamide (I-81);
N-(2-((2-(4Z,7Z,10Z,13Z,16Z,19Z)-docosa-4,7,10,13,16,19-hexaenamidoethyl)(methyl)amino)ethyl)-6-ethylnicotinamide (I-82);
N-(2-(2-(2-(4Z,7Z,10Z,13Z,16Z,19Z)-docosa-4,7,10,13,16,19-hexaenamidoethyl)disulfanyl)ethyl)-6-ethylnicotinamide (I-83);
6-chloro-N-(2-(2-(4Z,7Z,10Z,13Z,16Z,19Z)-docosa-4,7,10,13,16,19-hexaenamidoethoxy)ethyl)nicotinamide (I-84);
6-chloro-N-(2-((2-(4Z,7Z,10Z,13Z,16Z,19Z)-docosa-4,7,10,13,16,19-hexaenamidoethyl)(methyl)amino)ethyl)nicotinamide (I-85);
6-chloro-N-(2-(2-(2-(4Z,7Z,10Z,13Z,16Z,19Z)-docosa-4,7,10,13,16,19-hexaenamidoethyl)disulfanyl)ethyl)nicotinamide (I-86);
6-cyano-N-(2-(2-(4Z,7Z,10Z,13Z,16Z,19Z)-docosa-4,7,10,13,16,19-hexaenamidoethoxy)ethyl)nicotinamide (I-87);
6-cyano-N-(2-((2-(4Z,7Z,10Z,13Z,16Z,19Z)-docosa-4,7,10,13,16,19-hexaenamidoethyl)(methyl)amino)ethyl)nicotinamide (I-88); and
6-cyano-N-(2-(2-(2-(4Z,7Z,10Z,13Z,16Z,19Z)-docosa-4,7,10,13,16,19-hexaenamidoethyl)disulfanyl)ethyl)nicotinamide (I-89).

In other illustrative embodiments, compounds of Formula II are as set forth below:
1-((4Z,7Z,10Z,13Z,16Z,19Z)-docosa-4,7,10,13,16,19-hexaenoyloxy)ethyl nicotinate (II-1);
1-((5Z,8Z,11Z,14Z,17Z)-icosa-5,8,11,14,17-pentaenoyloxy)ethyl nicotinate (II-2);
1-((5Z,8Z,11Z,14Z,17Z)-icosa-5,8,11,14,17-pentaenoyloxy)cyclopropyl nicotinate (II-3);
4-((4Z,7Z,10Z,13Z,16Z,19Z)-docosa-4,7,10,13,16,19-hexaenoyloxy)-2-methylpentan-2-yl nicotinate (II-4);
3-((5Z,8Z,11Z,14Z,17Z)-icosa-5,8,11,14,17-pentaenoyloxy)-2-methylbutan-2-yl nicotinate (II-5);
4,5-dihydroxy-2-(((5Z,8Z,11Z,14Z,17Z)-icosa-5,8,11,14,17-pentaenoyloxy)methyl)tetrahydrofuran-3-yl nicotinate (II-6);
3-((5Z,8Z,11Z,14Z,17Z)-icosa-5,8,11,14,17-pentaenoyloxy)butan-2-yl nicotinate (II-7);
2-((5Z,8Z,11Z,14Z,17Z)-icosa-5,8,11,14,17-pentaenoyloxy)-3-(nicotinoyloxy)succinic acid (II-8);
1,1,2,2-tetrafluoro-2-((5Z,8Z,11Z,14Z,17Z)-icosa-5,8,11,14,17-pentaenoyloxy)ethyl nicotinate (II-9);
1,1,1,3-tetrafluoro-3-((5Z,8Z,11Z,14Z,17Z)-icosa-5,8,11,14,17-pentaenoyloxy)propan-2-yl nicotinate (II-10);
1-((4Z,7Z,10Z,13Z,16Z,19Z)-docosa-4,7,10,13,16,19-hexaenamido)ethyl nicotinate (II-11);
(5Z,8Z,11Z,14Z,17Z)-1-(nicotinamido)ethyl icosa-5,8,11,14,17-pentaenoate (II-12);
1-((5Z,8Z,11Z,14Z,17Z)-icosa-5,8,11,14,17-pentaenamido)cyclopropyl nicotinate (II-13);
4-((4Z,7Z,10Z,13Z,16Z,19Z)-docosa-4,7,10,13,16,19-hexaenamido)-2-methylpentan-2-yl nicotinate (II-14);
2-((5Z,8Z,11Z,14Z,17Z)-icosa-5,8,11,14,17-pentaenamido)-4-methylpentan-3-yl nicotinate (II-15);
4,5-dihydroxy-2-((5Z,8Z,11Z,14Z,17Z)-icosa-5,8,11,14,17-pentaenamidomethyl)tetrahydrofuran-3-yl nicotinate (II-16);
3-((5Z,8Z,11Z,14Z,17Z)-icosa-5,8,11,14,17-pentaenamido)butan-2-yl nicotinate (II-17)
2-((5Z,8Z,11Z,14Z,17Z)-icosa-5,8,11,14,17-pentaenamido)-3-(nicotinoyloxy)succinic acid (II-18);
1,1,2,2-tetrafluoro-2-((5Z,8Z,11Z,14Z,17Z)-icosa-5,8,11,14,17-pentaenamido)ethyl nicotinate (II-19);
3-fluoro-3-((5Z,8Z,11Z,14Z,17Z)-icosa-5,8,11,14,17-pentaenamido)-2-(nicotinoyloxy)propanoic acid (II-20); and
1,1,1,3-tetrafluoro-3-((5Z,8Z,11Z,14Z,17Z)-icosa-5,8,11,14,17-pentaenamido)propan-2-yl nicotinate (II-21).

Methods for Using Fatty Acid Niacin Derivatives

The invention also includes methods for treating metabolic diseases such as the treatment or prevention of metabolic diseases including atherosclerosis, dyslipidemia, coronary heart disease, hypercholesterolemia, Type 2 diabetes, elevated cholesterol, metabolic syndrome and cardiovascular disease.

In one embodiment, the method comprises contacting a cell with a fatty acid niacin derivative in an amount sufficient to decrease the release of triglycerides or VLDL or LDL or cause an increase in reverse cholesterol transport or increase HDL concentrations.

Also provided in the invention is a method for inhibiting, preventing, or treating a metabolic disease, or symptoms of a metabolic disease, in a subject. Examples of such disorders include, but are not limited to atherosclerosis, dyslipidemia, hypertriglyceridemia, hypertension, heart failure, cardiac arrhythmias, low HDL levels, high LDL levels, sudden death, stable angina, coronary heart disease, acute myocardial infarction, secondary prevention of myocardial infarction, cardiomyopathy, endocarditis, type 2 diabetes, insulin resistance, impaired glucose tolerance, hypercholesterolemia, stroke, hyperlipidemia, hyperlipoproteinemia, chronic kidney disease, intermittent claudication, hyperphosphatemia, carotid atherosclerosis, peripheral arterial disease, diabetic nephropathy, hypercholesterolemia in HIV infection, acute coronary syndrome (ACS), non-alcoholic fatty liver disease, arterial occlusive diseases, cerebral arteriosclerosis, cerebrovascular disorders, myocardial ischemia, and diabetic autonomic neuropathy.

In some embodiments, the subject is administered an effective amount of a fatty acid niacin derivative.

The invention also includes pharmaceutical compositions useful for treating or preventing a metabolic disease, or for inhibiting a metabolic disease, or more than one of these activities. The compositions can be suitable for internal use and comprise an effective amount of a fatty acid niacin derivative and a pharmaceutically acceptable carrier. The fatty acid niacin derivatives are especially useful in that they demonstrate very low peripheral toxicity or no peripheral toxicity.

The fatty acid niacin derivatives can each be administered in amounts that are sufficient to treat or prevent a metabolic disease or prevent the development thereof in subjects.

Administration of the fatty acid niacin derivatives can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, all using forms well known to those skilled in the pharmaceutical arts.

Illustrative pharmaceutical compositions are tablets and gelatin capsules comprising a fatty acid niacin derivative and a pharmaceutically acceptable carrier, such as: a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, alginic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the fatty acid niacin derivative is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the fatty acid niacin derivatives.

The fatty acid niacin derivatives can be also formulated as a suppository that can be prepared from fatty emulsions or suspensions; using polyalkylene glycols such as propylene glycol, as the carrier.

The fatty acid niacin derivatives can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564, the contents of which are herein incorporated by reference in their entirety.

Fatty acid niacin derivatives can also be delivered by the use of monoclonal antibodies as individual carriers to which the fatty acid niacin derivatives are coupled. The fatty acid niacin derivatives can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the fatty acid niacin derivatives can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, fatty acid niacin derivatives are not covalently bound to a polymer, e.g., a polycarboxylic acid polymer, or a polyacrylate.

Parenteral injectable administration is generally used for subcutaneous, intramuscular or intravenous injections and infusions. Injectables can be prepared in conventional forms, either as liquid solutions or suspensions or solid forms suitable for dissolving in liquid prior to injection.

Compositions can be prepared according to conventional mixing, granulating or coating methods, respectively, and the present pharmaceutical compositions can contain from about 0.1% to about 80%, from about 5% to about 60%, or from about 1% to about 20% of the fatty acid niacin derivative by weight or volume.

The dosage regimen utilizing the fatty acid niacin derivative is selected in accordance with a variety of factors including type, species, age, weight, sex and medical condition of the patient; the severity of the condition to be treated; the route of administration; the renal or hepatic function of the patient; and the particular fatty acid niacin derivative employed. A physician or veterinarian of ordinary skill in the art can readily determine and prescribe the effective amount of the drug required to prevent, counter or arrest the progress of the condition.

Effective dosage amounts of the present invention, when used for the indicated effects, range from about 20 mg to about 5,000 mg of the fatty acid niacin derivative per day. Compositions for in vivo or in vitro use can contain about 20, 50, 75, 100, 150, 250, 500, 750, 1,000, 1,250, 2,500, 3,500, or 5,000 mg of the fatty acid niacin derivative. In one embodiment, the compositions are in the form of a tablet that can be scored. Effective plasma levels of the fatty acid niacin derivative can range from about 0.002 mg to about 100 mg per kg of body weight per day. Appropriate dosages of the fatty acid niacin derivatives can be determined as set forth in Goodman, L. S.; Gilman, A. *The Pharmacological Basis of Therapeutics*, 5th ed.; MacMillan: New York, 1975, pp. 201-226.

Fatty acid niacin derivatives can be administered in a single daily dose, or the total daily dosage can be administered in divided doses of two, three or four times daily. Furthermore, fatty acid niacin derivatives can be administered in intranasal form via topical use of suitable intranasal vehicles, or via transdermal routes, using those forms of transdermal skin patches well known to those of ordinary skill in that art. To be administered in the form of a transdermal delivery system, the dosage administration can be continuous rather than intermittent throughout the dosage regimen. Other illustrative topical preparations include creams, ointments, lotions, aerosol sprays and gels, wherein the concentration of the fatty acid niacin derivative ranges from about 0.1% to about 15%, w/w or w/v.

Methods of Making

Methods for Making the Fatty Acid Niacin Derivatives

Examples of synthetic pathways useful for making fatty acid niacin derivatives of Formula I are set forth in the Examples below and generalized in Schemes 1-13.

Scheme 1

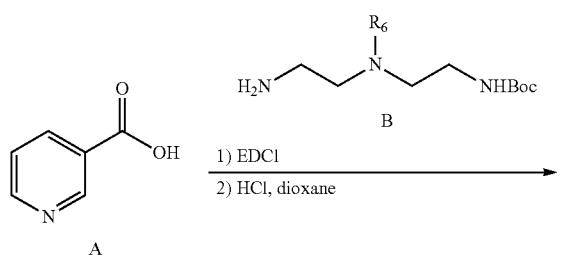

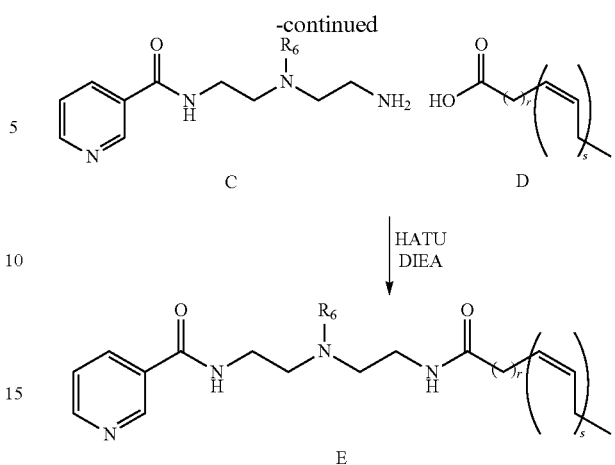

wherein $R_6$, r, and s are as defined above.

The mono-BOC protected amine of the formula B can be obtained from commercial sources or prepared according to the procedures outlined in Krapcho et al. *Synthetic Communications* 1990, 20, 2559-2564. Compound A can be amidated with the amine B using a coupling reagent such as DCC, CDI, EDC, or optionally with a tertiary amine base and/or catalyst, e.g., DMAP, followed by deprotection of the BOC group with acids such as TFA or HCl in a solvent such as $CH_2Cl_2$ or dioxane to produce the coupled compound C. Activation of compound C with a coupling agent such as HATU in the presence of an amine such as DIEA followed by addition of a fatty acid of formula D affords compounds of the formula E.

Scheme 2

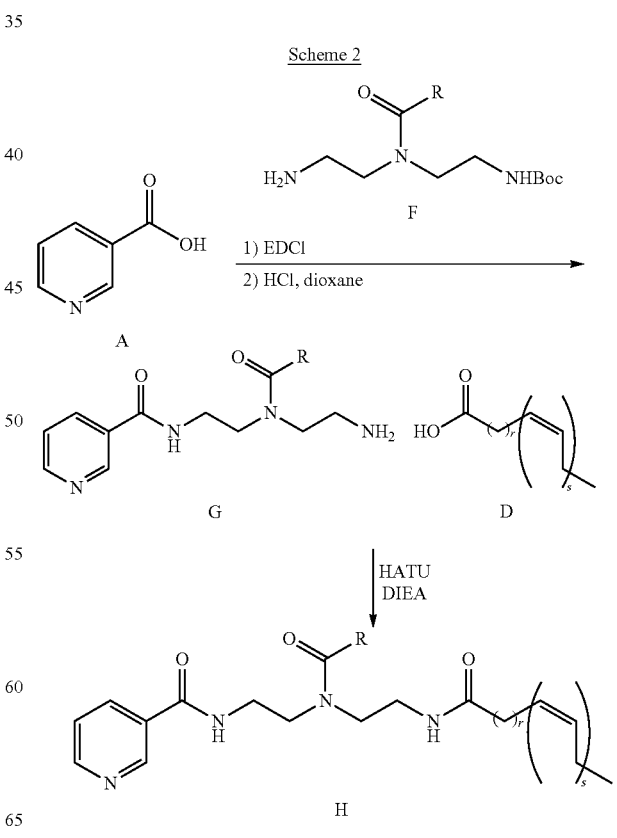

wherein R, r, and s are as defined above.

The acylated amine of the formula F can be prepared using the procedures outlined in Andruszkiewicz et al. *Synthetic Communications* 2008, 38, 905-913. Compound A can be amidated with the amine F using a coupling reagent such as DCC, CDI, EDC, or optionally with a tertiary amine base and/or catalyst, e.g., DMAP, followed by deprotection of the BOC group with acids such as TFA or HCl in a solvent such as $CH_2Cl_2$ or dioxane to produce the coupled compound G. Activation of compound G with a coupling agent such as HATU in the presence of an amine such as DIEA followed by addition of a fatty acid of formula D affords compounds of the formula H.

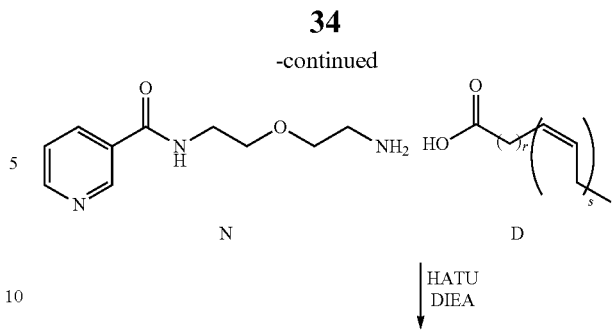

Scheme 3

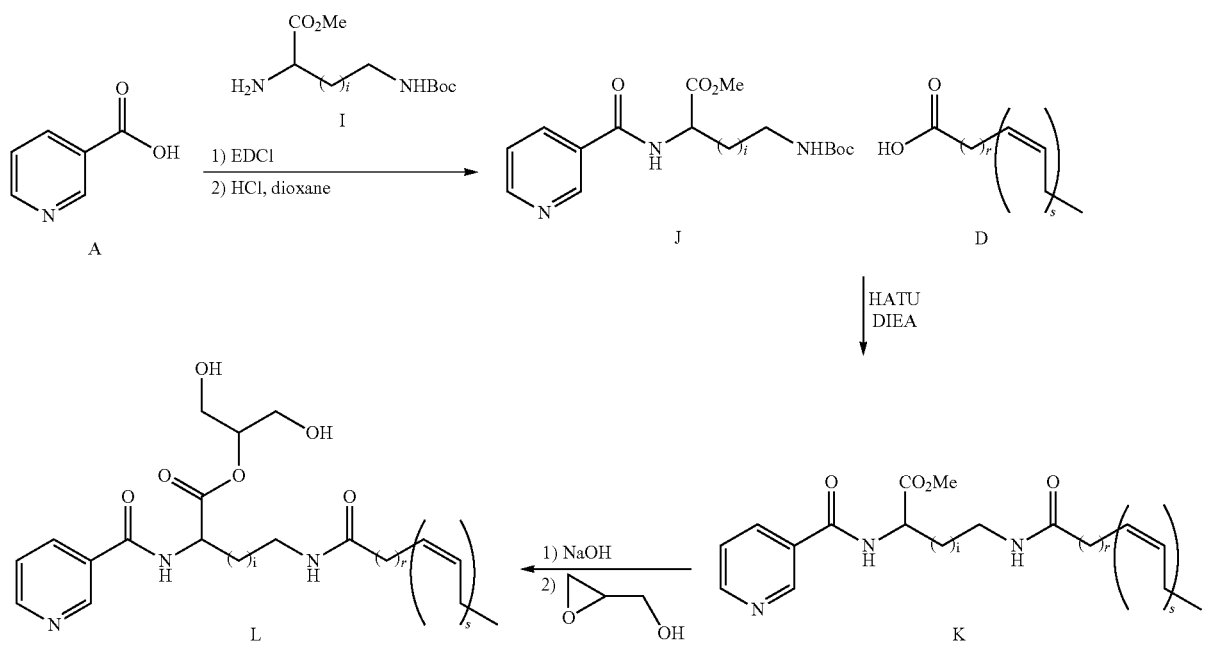

wherein r and s are as defined above.

Compound A can be amidated with the corresponding amine I (where i=0, 1, 2 or 3) using a coupling reagent such as DCC, CDI, EDC, or optionally with a tertiary amine base and/or catalyst, e.g., DMAP, followed by deprotection of the BOC group with acids such as TFA or HCl in a solvent such as $CH_2Cl_2$ or dioxane to produce the coupled compound J. Activation of compound J with a coupling agent such as HATU in the presence of an amine such as DIEA followed by addition of a fatty acid of formula D affords compounds of the formula K. Hydrolysis of the ester under basic conditions such as NaOH or LiOH produces the corresponding acid, which can be coupled with glycidol to afford compounds of the formula L.

Scheme 4

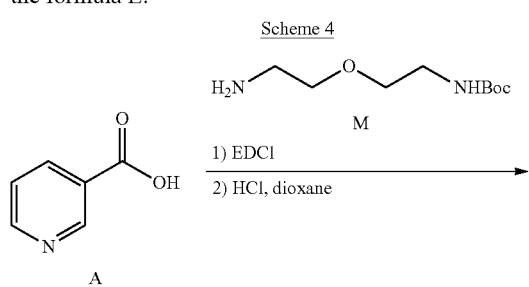

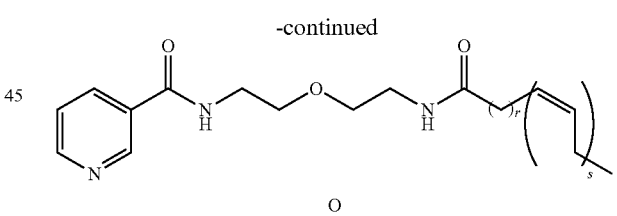

wherein r and s are as defined above.

The amine M can be prepared according to the procedures outlined in Dahan et al. *J. Org. Chem.* 2007, 72, 2289-2296. Compound A can be coupled with the amine M using a coupling reagent such as DCC, CDI, EDC, or optionally with a tertiary amine base and/or catalyst, e.g., DMAP, followed by deprotection of the BOC group with acids such as TFA or HCl in a solvent such as $CH_2Cl_2$ or dioxane to produce the coupled compound N. Activation of compound N with a coupling agent such as HATU in the presence of an amine such as DIEA followed by addition of a fatty acid of formula D affords compounds of the formula O.

Scheme 5

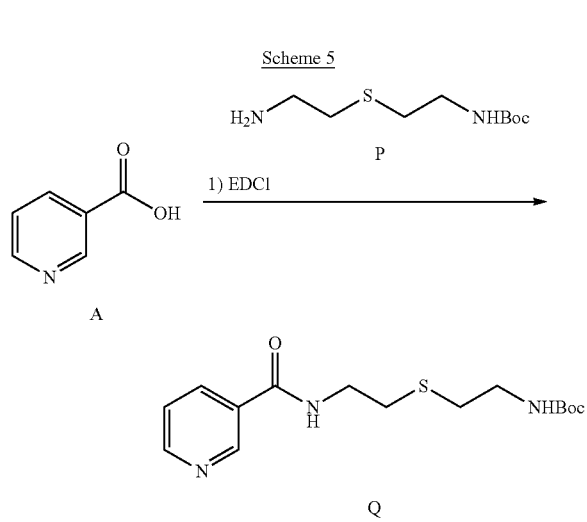

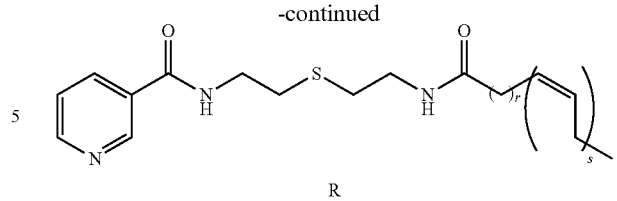

wherein r and s are as defined above.

Compound A can be amidated with the commercially available amine P using a coupling reagent such as DCC, CDI, EDC, or optionally with a tertiary amine base and/or catalyst, e.g., DMAP, to afford compound Q. The BOC group in compound Q can be removed with acids such as TFA or HCl in a solvent such as $CH_2Cl_2$ or dioxane and the resulting amine can be coupled with a fatty acid of formula D using a coupling agent such as HATU in the presence of an amine such as DIEA to afford compounds of the formula R. To those skilled in the art, the sulfur group in formula Q can be oxidized to the corresponding sulfoxide or sulfone using an oxidizing agent such as $H_2O_2$ or oxone.

Scheme 6

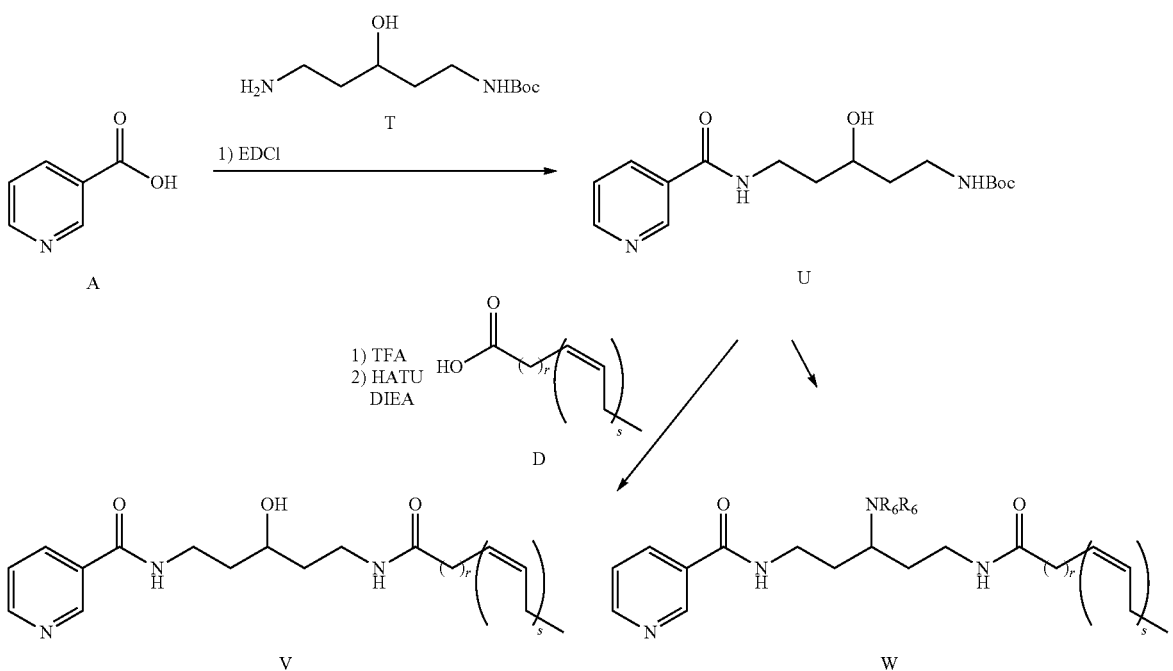

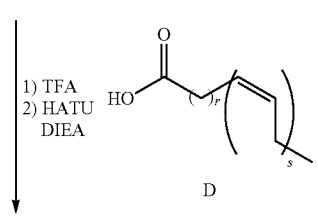

wherein $R_6$, r, and s are as defined above.

The amine T can be prepared from the commercially available diamine according to the procedures outlined in Dahan et al. *J. Org. Chem.* 2007, 72, 2289-2296. Compound A can be amidated with the amine T using a coupling reagent such as DCC, CDI, EDC, or optionally with a tertiary amine base and/or catalyst, e.g., DMAP, to afford compound U. The BOC group of compound U can be removed with acids such as TFA or HCl in a solvent such as $CH_2Cl_2$ or dioxane and the resulting amine can be coupled with a fatty acid of formula D using HATU in the presence of an amine such as DIEA to afford compounds of the formula V. To those skilled in the art, the hydroxyl group in compound U can be further acylated or converted to an amino group by standard mesylation chemistry followed by displacement with sodium azide and hydrogenation over a catalyst such as Pd/C. The amine can be further acylated or alkylated, followed by the removal of the BOC group. The resulting amine can be coupled with a fatty acid of the formula D to afford compounds of the formula W.

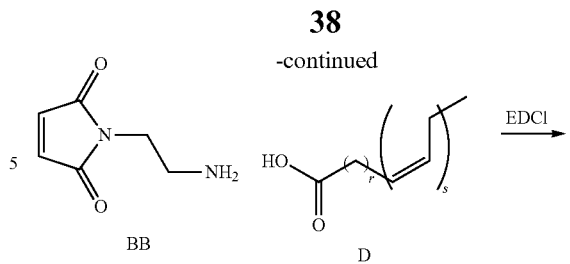

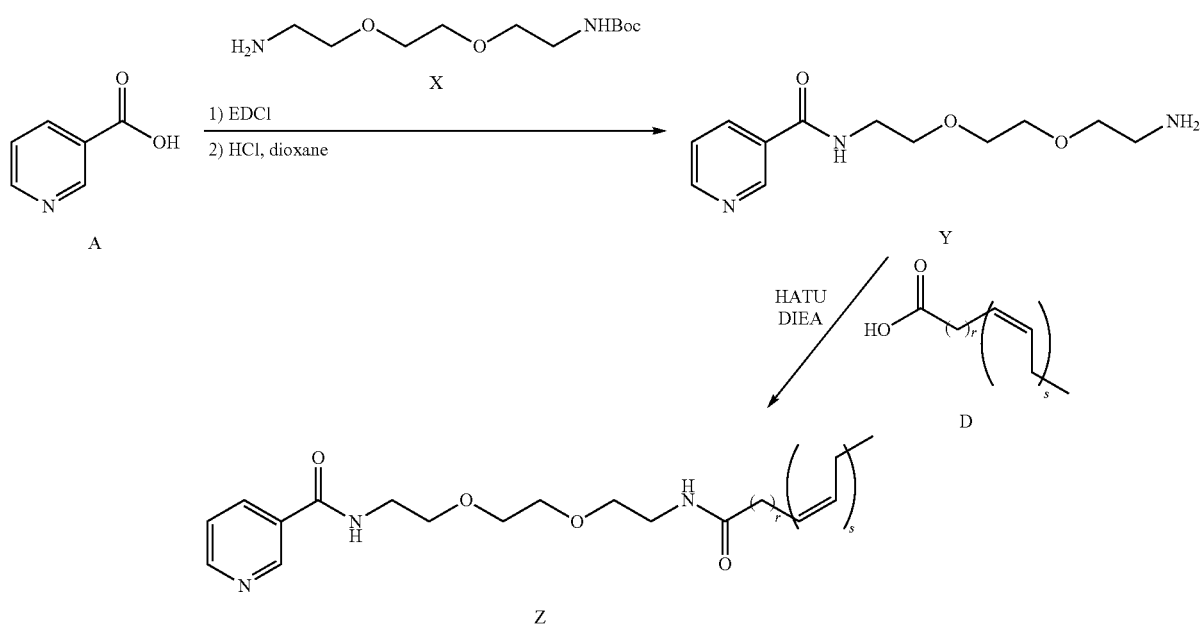

wherein r and s are as defined above.

Compound A can be amidated with the commercially available amine X using a coupling reagent such as DCC, CDI, EDC, optionally with a tertiary amine base and/or catalyst, e.g., DMAP to afford compound Y. The BOC group in compound Y can be removed with acids such as TFA or HCl in a solvent such as $CH_2Cl_2$ or dioxane. The resulting amine can be coupled with a fatty acid of the formula D using a coupling agent such as HATU in the presence of an amine such as DIEA to afford compounds of the formula Z.

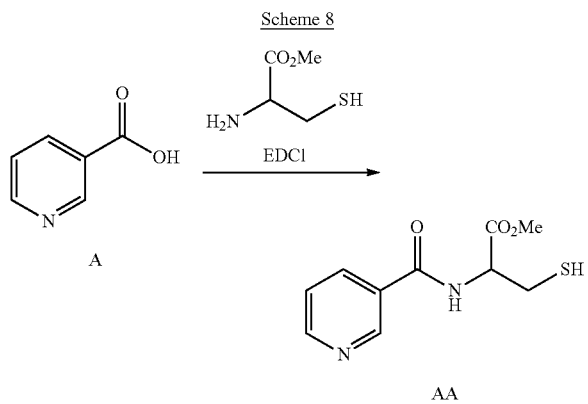

wherein r and s are as defined above.

Compound A can be amidated with the commercially available cysteine methyl ester using a coupling reagent such as DCC, CDI, EDC, or optionally with a tertiary amine base and/or catalyst, e.g., DMAP, to afford compound AA. The commercially available maleimide derivative BB can be coupled with a fatty acid of the formula D using a coupling agent such as HATU or EDCI to afford compounds of the formula CC. Compound AA can be coupled to compounds of the formula CC in a solvent such as acetonitrile to afford compounds of the formula DD.

Scheme 9

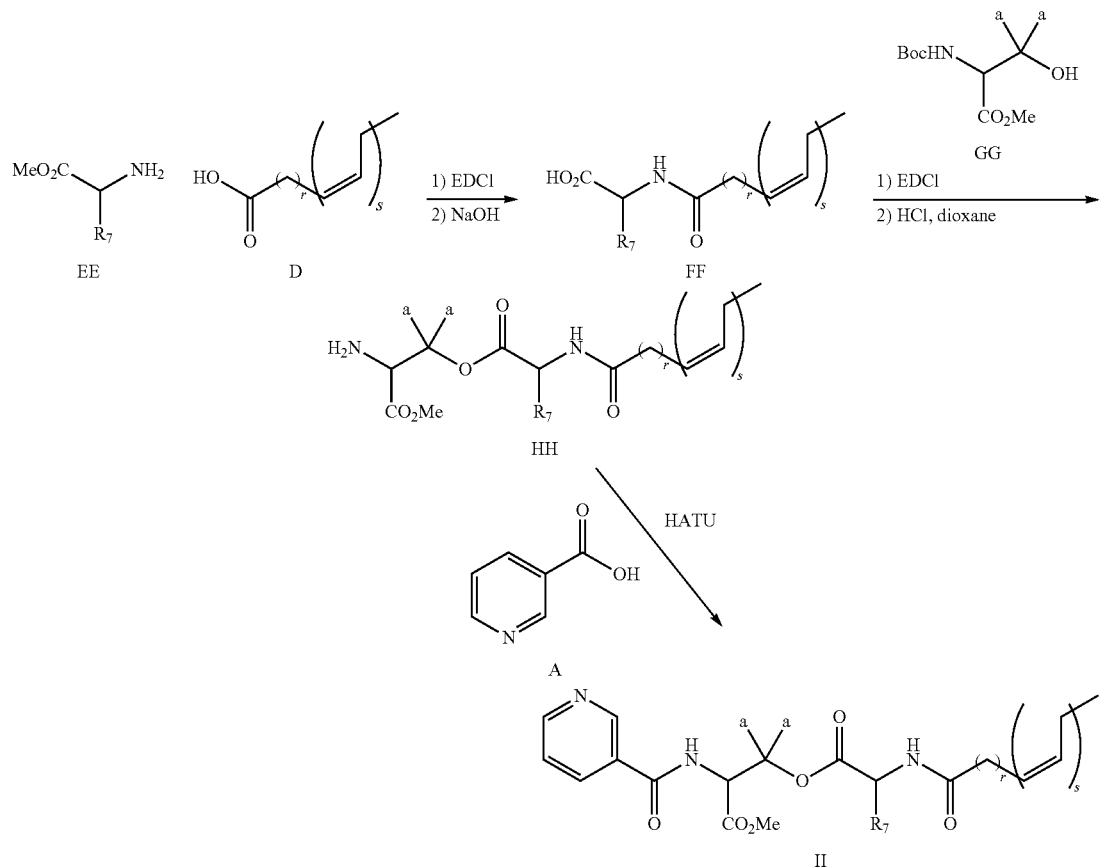

wherein $R_7$, a, r, and s are as defined above.

The commercially available amino acid esters EE can be coupled with a fatty acid of the formula D using a coupling agent such as EDCI or HATU, followed by alkaline hydrolysis of the methyl ester to afford compounds of the formula FF. Compounds of the formula FF can be coupled with the commercially available BOC-amino acid derivatives GG using a coupling agent such as EDCI or HATU. The BOC group can be removed by treatment with acids such as TFA or HCl to afford compounds of the formula HH which can then be coupled with compound A to afford compounds of the formula II.

Examples of synthetic pathways useful for making fatty acid niacin derivatives of Formula II are set forth in the Examples below and generalized in Schemes 10-13.

Scheme 10

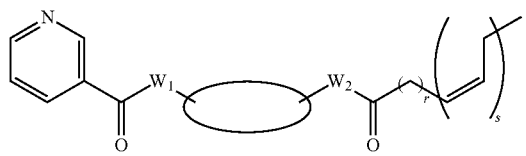

In general terms, the fatty acid niacin derivatives are comprised of niacin, a fatty acid and a linker represented by the oval above which is comprised of a suitably functionalized C1-C5 alkyl chain which provides steric bulk that will modulate the rate of hydrolysis of the ester or amide bond.

Scheme 11

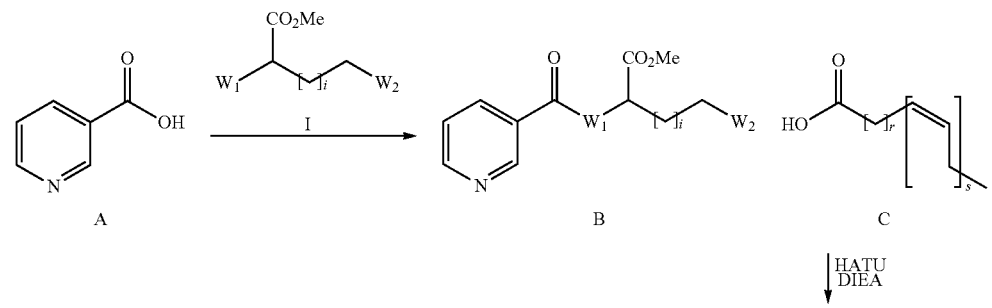

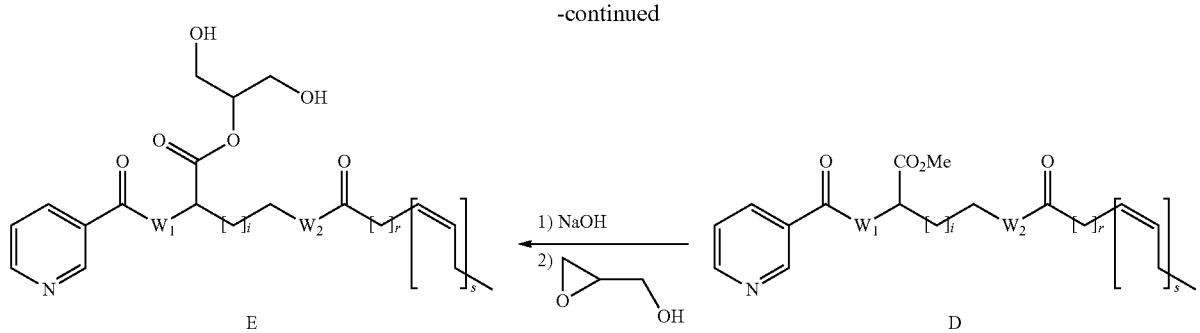

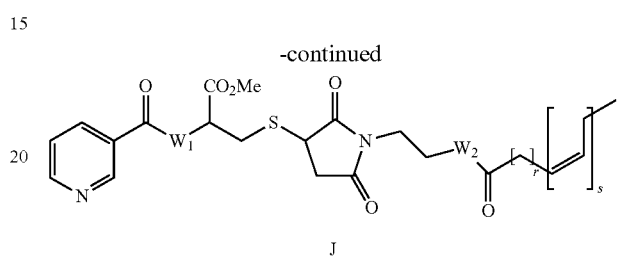

wherein r and s are as defined above, and i is 0-3.

Compound A can be coupled with the building block I (where i=0, 1, 2 or 3) using a coupling reagent such as DCC, CDI, EDC, or optionally with a tertiary amine base and/or catalyst, e.g., DMAP to provide the coupled compound B. Activation of compound B with a coupling agent such as HATU in the presence of an amine such as DIEA followed by addition of a fatty acid of formula C affords compounds of the formula D. Hydrolysis of the ester under basic conditions such as NaOH or LiOH produces the corresponding acid, which can be coupled with glycidol to afford compounds of the formula E.

wherein r and s are as defined above.

Compound A can be coupled with the commercially available cysteine methyl ester analog using a coupling reagent such as DCC, CDI, EDC, or optionally with a tertiary amine base and/or catalyst, e.g., DMAP, to afford compound F. The commercially available maleimide derivative G can be coupled with a fatty acid of the formula C using a coupling agent such as HATU or EDCI to afford compounds of the formula H. Compound F can be coupled to compounds of the formula H in a solvent such as acetonitrile to afford compounds of the formula J.

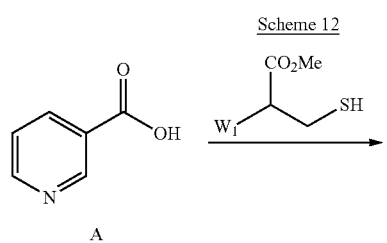

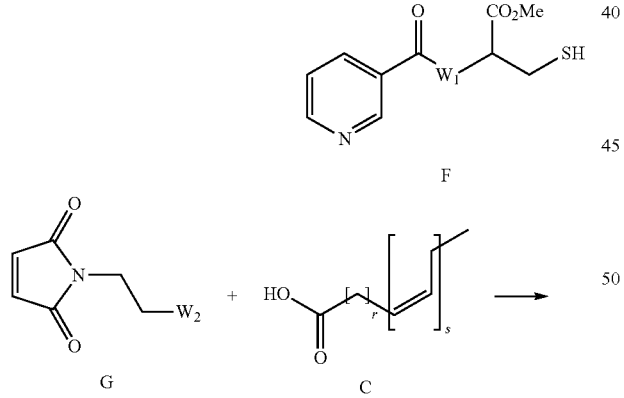

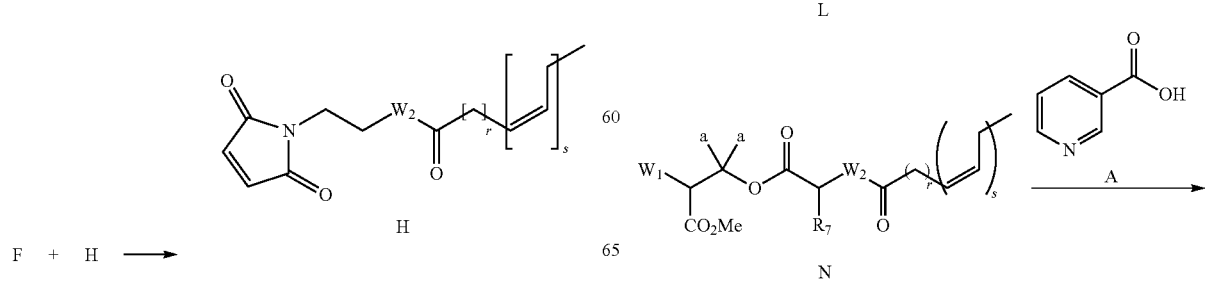

-continued

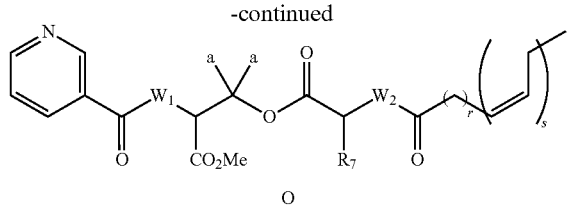

wherein $R_7$, a, r, and s are as defined above.

The commercially available acid esters K can be coupled with a fatty acid of the formula C using a coupling agent such as EDCI or HATU, followed by alkaline hydrolysis of the methyl ester to afford compounds of the formula L. Compounds of the formula L can be coupled with the commercially available alcohol derivatives M using a coupling agent such as EDCI or HATU to afford compounds of the formula N which can then be coupled with compound A to afford compounds of the formula O.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Example 1

Effect of Fatty Acid Niacin Derivatives on ApoB Secretion in HepG2 Cells

Niacin has been reported to increase serum levels of HDL to LDL cholesterol in vivo. Similarly, niacin has been reported to increase the secretion of ApoA1 (Jin, F-Y. et al. *Arterioscler. Thromb. Vasc. Biol.* 1997, 17 (10), 2020-2028) while inhibiting the secretion of ApoB (Jin, F-Y. et al. *Arterioscler. Thromb. Vasc. Biol.* 1999, 19, 1051-1059) in the media supernatants of HepG2 cultures. Independently, DHA has been demonstrated to lower ApoB as well (Pan, M. et al. *J. Clin. Invest.* 2004, 113, 1277-1287) by a very different mechanism. Thus, the secretion of ApoB from HepG2 cells possesses utility as a cell based read-out for niacin-DHA conjugates, as well as derivatives of same.

HepG2 cells (ATCC) are seeded at 10,000 cells per well in 96 well plates. After adhering overnight, growth media (10% FBS in DMEM) is removed and cells are serum starved for 24 hours in DMEM containing 0.1% fatty acid free bovine serum albumin (BSA, Sigma). Cells are then treated with a compound. Niacin at 5 mM is used as a positive control. All treatments are performed in triplicate. Simultaneous with compound treatment, ApoB secretion is stimulated with addition of 0.1 oleate complexed to fatty acid free BSA in a 5:1 molar ratio. Incubation with a compound and oleate is conducted for 24 hours. Media supernatants are removed and ApoB concentrations are measured using ELISA kits (Mabtech AB). Percent inhibition of ApoB secretion is determined by normalizing data to vehicle treated wells. For a given compound, an $IC_{50}$ (concentration at which 50% of ApoB secretion is inhibited) can also be determined by using a 4 parameter-fit inhibition curve model (Graph Pad Prism®). In each experiment, cell viability is determined using the ATPlite 1-Step kit (Perkin Elmer), such that compound effects due to cytotoxicity can be monitored.

The fatty acid niacin conjugate 1-7 was evaluated in HepG2 cells at 3 concentrations (50, 100 and 200 µM). The level of ApoB secretion was compared to that of niacin, evaluated at 5 mM concentration. Compared to niacin, the fatty acid niacin conjugate 1-7 showed significant inhibition of ApoB at a much lower drug concentration as shown in FIG. 1.

Example 2

Effect of Fatty Acid Niacin Derivatives on SREBP-1c Target Genes

Figure 2:
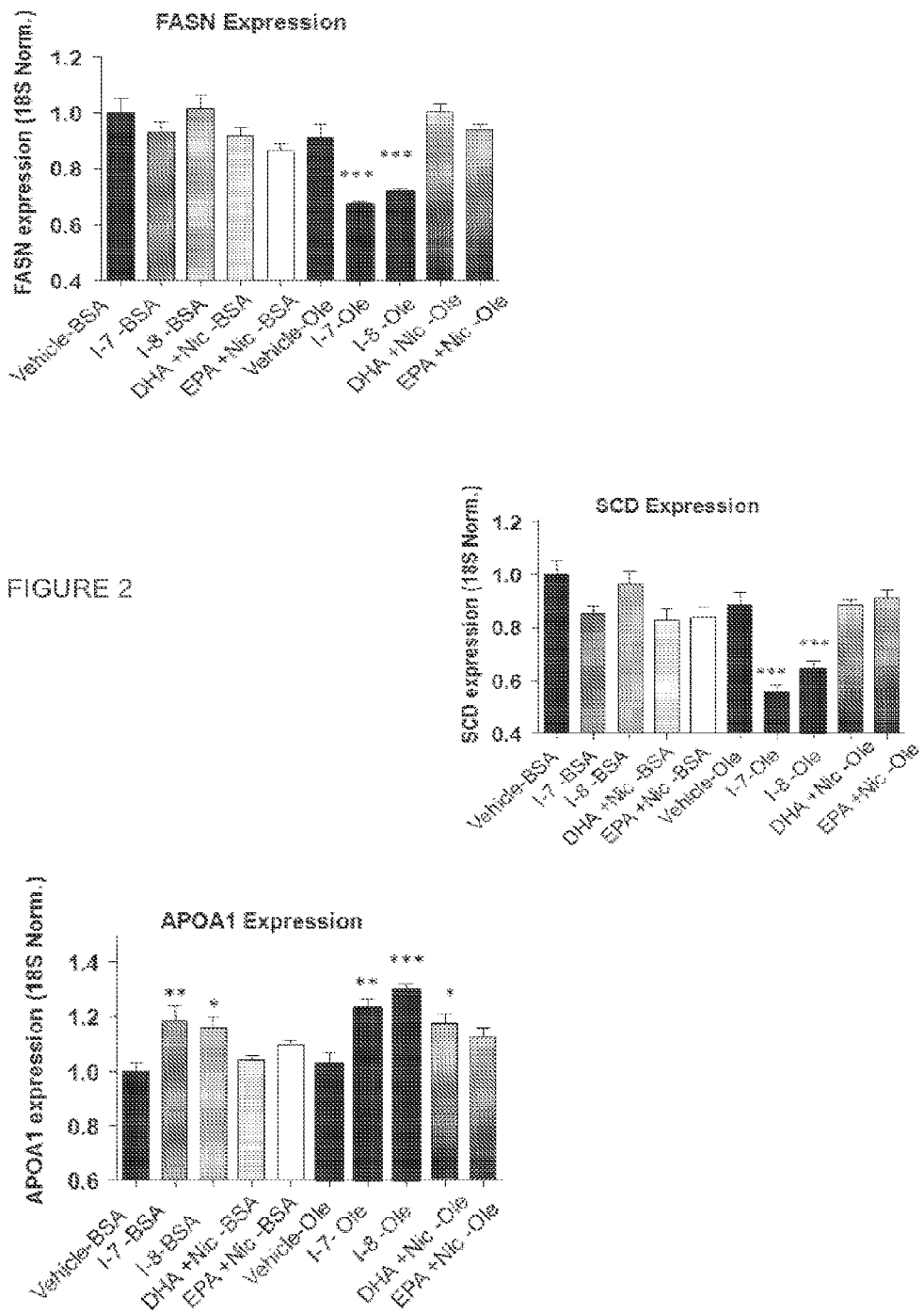
FIG. 2 is a depiction of the effect of fatty acid niacin derivatives on SREBP-1c target genes.

HepG2 cells (ATCC) were seeded at 20,000 cells per well in 96 well plates. After adhering overnight, growth media (10% FBS in DMEM) was removed and cells were serum starved for 24 hours in DMEM containing 1% fatty acid free bovine serum albumin (BSA, Sigma). Cells were then treated with one of four substances at a final concentration of 50 µM in 1% BSA or 0.1% oleate complexed to fatty acid free BSA in a 5:1 molar ratio (the four substances were compound I-7, compound I-8, a combination of free niacin and free DHA, or a combination of free niacin and free EPA). Cells were incubated for 6 hours and then washed with PBS. RNA was reverse-transcribed using the cells to cDNA reagents according to standard protocols (outlined in Applied Biosystem StepOne Real-time PCR protocols). Real time PCR of transcripts was performed with Taqman assays for the three specific genes FASN (fatty acid synthase), SCD (steroyl CoA desaturase) and ApoA1 (apolipoprotein A1). In all three cases, 185-VIC® was used as a normalization control. As shown in FIG. 2, statistically significant inhibition of FASN and SCD gene expression and an increase in ApoA1 gene expression were observed when HepG2 cells were stimulated with oleate in the presence of 50 µM of compound I-7 and compound I-8. The two groups containing a combination of either free niacin and free DHA or niacin and free EPA produced no significant changes in the expression of these three specific genes at a final concentration of 50 µM.

Compounds

The following non-limiting compound examples serve to illustrate further embodiments of the fatty acid niacin derivatives. It is to be understood that any embodiments listed in the Examples section are embodiments of the fatty acid niacin derivatives and, as such, are suitable for use in the methods and compositions described above.

Example 3

Preparation of N-(2-(4Z,7Z,10Z,13Z,16Z,19Z)-docosa-4,7,10,13,16,19-hexaenamidoethyl)nicotinamide (I-7)

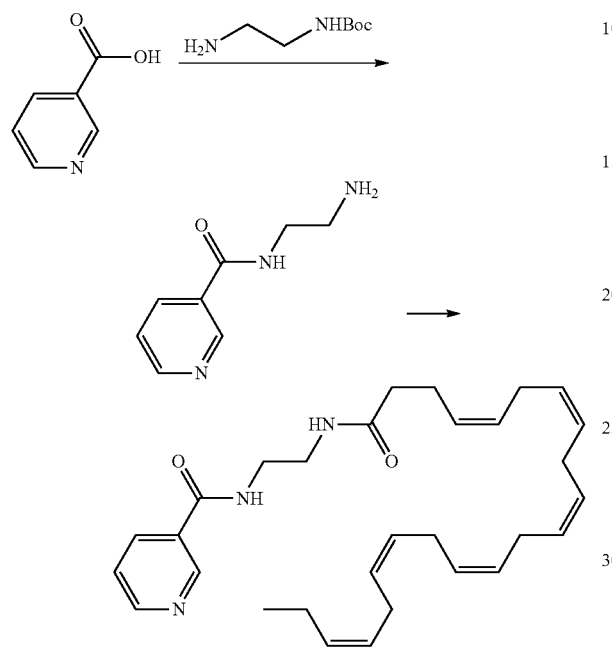

In a typical run, nicotinic acid (2.0 g, 16.2 mmol) was taken up in CH$_2$Cl$_2$ (20 mL) along with oxalyl chloride (1.4 mL, 16.2 mmol). After a few drops of DMF were added, the reaction mixture was stirred at room temperature until all the solids had dissolved and all gas evolution had ceased (1 h). This freshly prepared solution of the acid chloride was added dropwise at 0° C. to a solution containing tert-butyl 2-aminoethylcarbamate (2.6 g, 16.2 mmol) and Et$_3$N (3.4 mL, 24.2 mmol) in CH$_2$Cl$_2$ (200 mL). The resulting reaction mixture was warmed to room temperature and stirred for 2 h. It was then washed with brine, dried over Na$_2$SO$_4$, filtered and concentrated under reduced pressure. Purification by silica gel chromatography (CH$_2$Cl$_2$) afforded tert-butyl 2-(nicotinamido)ethylcarbamate (3.1 g, 74%).

tert-Butyl 2-(nicotinamido)ethylcarbamate (3.1 g, 11.7 mmol) was taken up in 25% TFA in CH$_2$Cl$_2$ (10 mL). The resulting reaction mixture was allowed to stand at room temperature for 1 h. At this point, a considerable amount of precipitate formed and the clear filtrate was removed. The remaining solids were dried to afford of the TFA salt of N-(2-aminoethyl)nicotinamide (1.6 g).

The TFA salt of N-(2-aminoethyl)nicotinamide (5.0 mmol) was taken up in CH$_3$CN (20 mL) along with (4Z,7Z,10Z,13Z,16Z,19Z)-docosa-4,7,10,13,16,19-hexaenoic acid (5.0 mmol), HATU (5.5 mmol) and DIEA (15 mmol). The resulting reaction mixture was stirred at room temperature for 2 h and diluted with EtOAc. The organic layer was washed with saturated aqueous NaHCO$_3$, brine, dried over Na$_2$SO$_4$, filtered and concentrated under reduced pressure. Purification by silica gel chromatography (5% MeOH—CH$_2$Cl$_2$) afforded N-(2-(4Z,7Z,10Z,13Z,16Z,19Z)-docosa-4,7,10,13, 16,19-hexaenamidoethyl)nicotinamide. MS calculated for C$_{30}$H$_{41}$N$_3$O$_2$: 475.32. found: [M+H]$^+$ 476.

Example 4

Preparation of N-(2-(5Z,8Z,11Z,14Z,17Z)-eicosa-5,8,11,14,17-pentaenamidoethyl)nicotinamide (I-8)

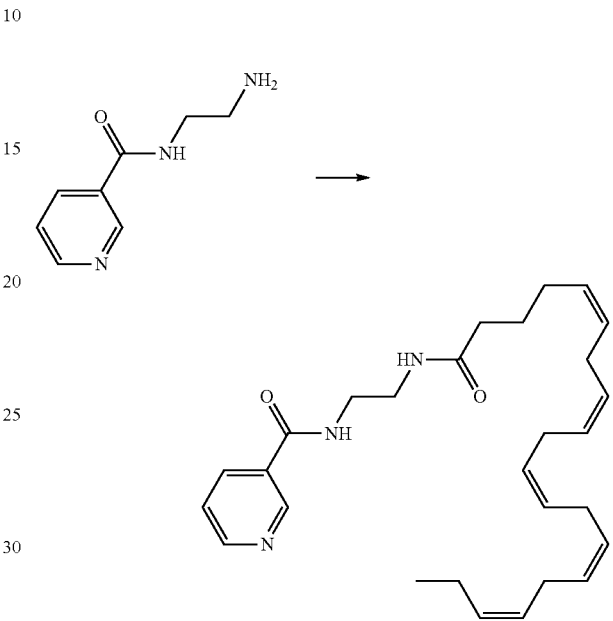

The TFA salt of N-(2-aminoethyl)nicotinamide (1.6 g, 5.7 mmol) was taken up in CH$_3$CN (15 mL) along with (5Z,8Z,11Z,14Z,17Z)-eicosa-5,8,11,14,17-pentaenoic acid (1.7 g, 5.7 mmol), HATU (2.4 g, 6.3 mmol) and DIEA (3 mL, 17 mmol). The resulting reaction mixture was stirred at room temperature for 2 h and diluted with EtOAc. The organic layer was washed with saturated aqueous NaHCO$_3$, brine, dried over Na$_2$SO$_4$, filtered and concentrated under reduced pressure. Purification by silica gel chromatography (5% MeOH—CH$_2$Cl$_2$) afforded N-(2-(5Z,8Z,11Z,14Z,17Z)-eicosa-5,8,11,14,17-pentaenamidoethyl)nicotinamide (1.6 g, 62%). MS calculated for C$_{28}$H$_{39}$N$_3$O$_2$: 449.3. found: [M+H]$^+$ 450.

Example 5

Preparation of N-(2-(2-(2-(4Z,7Z,10Z,13Z,16Z,19Z)-docosa-4,7,10,13,16,19-hexaenamidoethyl)disulfanyl)ethyl)nicotinamide (I-3)

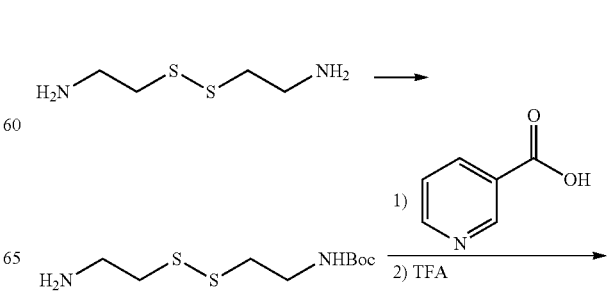

-continued

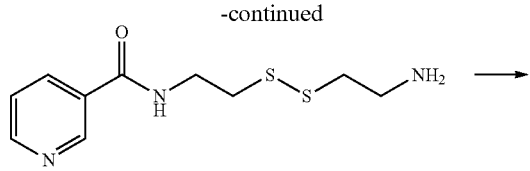

↓

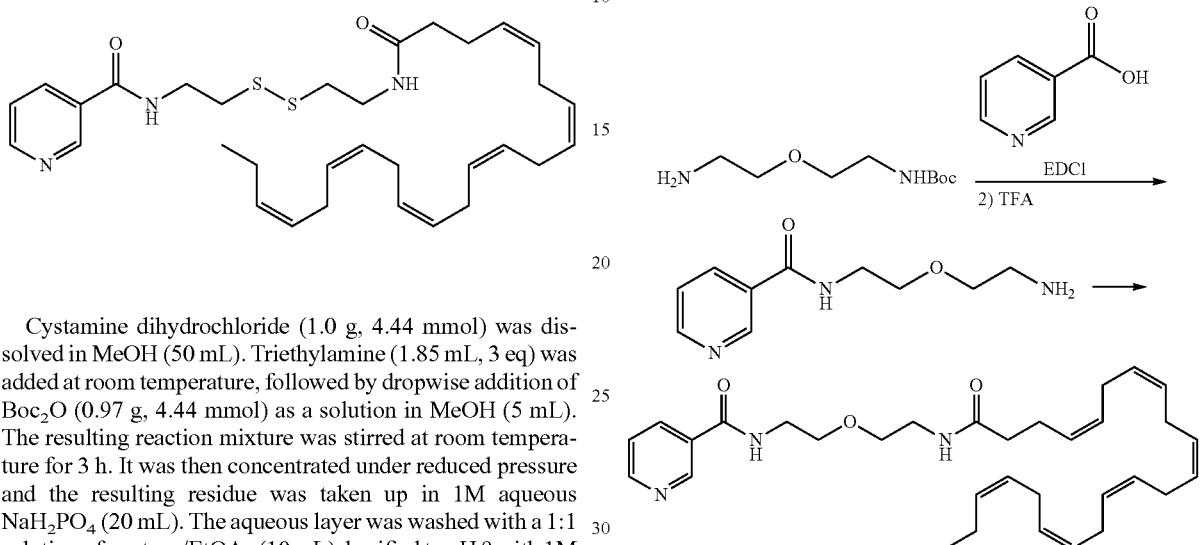

Cystamine dihydrochloride (1.0 g, 4.44 mmol) was dissolved in MeOH (50 mL). Triethylamine (1.85 mL, 3 eq) was added at room temperature, followed by dropwise addition of Boc$_2$O (0.97 g, 4.44 mmol) as a solution in MeOH (5 mL). The resulting reaction mixture was stirred at room temperature for 3 h. It was then concentrated under reduced pressure and the resulting residue was taken up in 1M aqueous NaH$_2$PO$_4$ (20 mL). The aqueous layer was washed with a 1:1 solution of pentane/EtOAc (10 mL), basified to pH 9 with 1M aqueous NaOH, and extracted with EtOAc. The combined organic layers were washed with brine, dried over Na$_2$SO$_4$, filtered and concentrated under reduced pressure to afford tert-butyl 2-(2-(2-aminoethyl)disulfanyl)ethylcarbamate (500 mg, 44%).

Separately, nicotinic acid (246 mg, 2.0 mmol) was taken up in CH$_3$CN (10 mL) along with tert-butyl 2-(2-(2-aminoethyl)disulfanyl)ethylcarbamate (503 mg, 2.0 mmol), EDCI (422 mg, 2.2 mmol). The resulting reaction mixture was stirred at room temperature for 4 h and then diluted with EtOAc. The organic layer was washed with dilute aqueous NaHCO$_3$, brine, dried over Na$_2$SO$_4$, filtered and concentrated under reduced pressure. Purification by silica gel chromatography (CH$_2$Cl$_2$) afforded tert-butyl 2-(2-(2-(nicotinamido)ethyl)disulfanyl)ethylcarbamate (400 mg, 56%).

tert-Butyl 2-(2-(2-(nicotinamido)ethyl)disulfanyl)ethylcarbamate (200 mg, 0.56 mmol) was taken up in 25% TFA in CH$_2$Cl$_2$ solution (5 mL) and allowed to stand at room temperature for 4 h. The reaction mixture was then concentrated under reduced pressure to afford the TFA salt of N-(2-(2-(2-aminoethyl)disulfanyl)ethyl)nicotinamide. This material was taken up in CH$_3$CN (10 mL) along with (4Z,7Z,10Z,13Z,16Z,19Z)-docosa-4,7,10,13,16,19-hexaenoic acid (184 mg, 0.56 mmol), HATU (234 mg, 0.62 mmol) and DIEA (0.30 mL). The resulting reaction mixture was stirred at room temperature for 2 h. It was then diluted with EtOAc and washed successively with saturated aqueous NaHCO$_3$ and brine. The organic layer was dried over Na$_2$SO$_4$, filtered and concentrated under reduced pressure. Purification by silica gel chromatography (5% MeOH—CH$_2$Cl$_2$) afforded (N-(2-(2-(2-(4Z,7Z,10Z,13Z,16Z,19Z)-docosa-4,7,10,13,16,19-hexaenamidoethyl)disulfanyl)ethyl)nicotinamide (300 mg, 86%). MS calculated for C$_{32}$H$_{45}$N$_3$O$_2$S$_2$: 567.3. found: [M+H]$^+$ 568.

Example 6

Preparation of N-(2-(2-(4Z,7Z,10Z,13Z,16Z,19Z)-docosa-4,7,10,13,16,19-hexaenamidoethoxy)ethyl)nicotinamide (I-1)

In a typical run, sodium hydroxide (400 mg, 10 mmol) was dissolved in MeOH (70 mL) and 2-(2-aminoethoxy)ethanamine dihydrochloride (1.0 g, 5.65 mmol) was added. The resulting reaction mixture was stirred at room temperature for 30 min. A solution containing Boc$_2$O (740 mg, 3.40 mmol) in THF (15 mL) was then added dropwise, at room temperature, over a period of 15 min. The resulting reaction mixture was stirred at room temperature for 18 h. It was then concentrated under reduced pressure. The resulting residue was taken up in CH$_2$Cl$_2$ (200 mL) and stirred vigorously at room temperature for 4 h. The mixture was filtered and the filtrate was concentrated under reduced pressure to afford tert-butyl 2-(2-aminoethoxy)ethylcarbamate (850 mg, 74%).

tert-Butyl 2-(2-aminoethoxy)ethylcarbamate (420, 2.06 mmol) was then taken up in CH$_3$CN (20 mL) along with nicotinic acid (253 mg, 2.06 mmol) and EDCI (434 mg, 2.3 mmol). The resulting reaction mixture was stirred at room temperature for 18 h. It was then diluted with EtOAc (20 mL), washed with saturated aqueous NaHCO$_3$, brine, dried over Na$_2$SO$_4$, filtered and concentrated under reduced pressure. The resulting residue was purified by silica gel chromatography (9:1 CH$_2$Cl$_2$/MeOH) to afford tert-butyl 2-(2-(nicotinamido)ethoxy)ethylcarbamate (280 mg, 44%). MS calculated for C$_{15}$H$_{23}$N$_3$O$_4$: 309.17. found: [M+H]$^+$ 310.

tert-Butyl 2-(2-(nicotinamido)ethoxy)ethylcarbamate (140 mg, 0.453 mmol) was taken up in 25% TFA in CH$_2$Cl$_2$ (10 mL). The reaction mixture was allowed to stand at room temperature for 2 h and then concentrated under reduced pressure to afford the TFA salt of N-(2-(2-aminoethoxy)ethyl)nicotinamide. This material was then taken up in CH$_3$CN (10 mL) along with (4Z,7Z,10Z,13Z,16Z,19Z)-docosa-4,7,10,13,16,19-hexaenoic acid (148 mg, 0.453 mmol), HATU (190 mg, 0.498 mmol) and DIEA (0.24 mL). The resulting reaction mixture was stirred at room temperature for 2 h. It was then diluted with EtOAc and washed successively with saturated aqueous NaHCO₃ and brine. The organic layer was dried over Na₂SO₄, filtered and concentrated under reduced pressure. Purification by silica gel chromatography (9:1 CH₂Cl₂/MeOH) afforded N-(2-(2-(4Z,7Z,10Z,13Z,16Z,19Z)-docosa-4,7,10,13,16,19-hexaenamidoethoxy)ethyl)nicotinamide (75 mg, 31%). MS calculated for $C_{31}H_{46}N_2O_5$: 526.34. found: [M+H]⁺ 527.

Example 7

Preparation of N-(2-β2-(4Z,7Z,10Z,13Z,16Z,19Z)-docosa-4,7,10,13,16,19-hexaenamidoethyl)(methyl)amino)ethyl)nicotinamide (I-2)

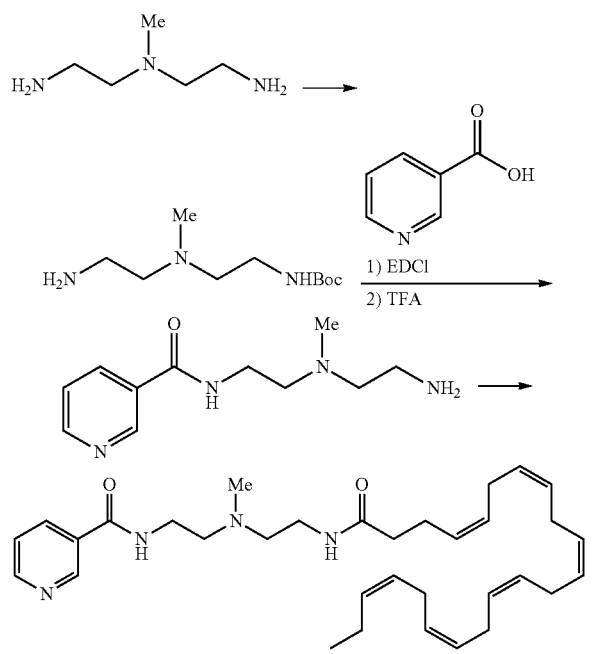

N1-(2-Aminoethyl)-N-1-methylethane-1,2-diamine (5.0 g, 42.7 mmol) was dissolved in CH₂Cl₂ (100 mL) and cooled to 0° C. A solution of Boc₂O (0.93 g, 4.27 mmol) in CH₂Cl₂ (10 mL) was then added dropwise at 0° C. over a period of 15 min. The resulting reaction mixture was stirred at 0° C. for 30 min and then warmed to room temperature. After stirring at room temperature for 2 h, the reaction mixture was diluted with CH₂Cl₂ (100 mL). The organic layer was washed with brine (3×25 mL), dried over Na₂SO₄, filtered and concentrated under reduced pressure to afford tert-butyl 2-((2-aminoethyl)(methyl)amino)ethylcarbamate (1.1 g).

tert-Butyl 2-((2-aminoethyl)(methyl)amino)ethylcarbamate (400 mg, 1.84 mmol) was taken up in CH₃CN (10 mL) along with nicotinic acid (227 mg, 1.84 mmol) and EDCI (353 mg, 2.02 mmol). The resulting reaction mixture was stirred at room temperature for 18 h and then diluted with EtOAc. The organic layer was washed with saturated aqueous NaHCO₃, brine, dried over Na₂SO₄, filtered and concentrated under reduced pressure. The resulting residue was purified by silica gel chromatography (5% MeOH—CH₂Cl₂) to afford tert-butyl 2-(methyl(2-(nicotinamido)ethyl)amino)ethylcarbamate (180 mg, 30%). MS calculated for $C_{16}H_{26}N_4O_3$: 322.2. found: [M+H]⁺ 323.

tert-Butyl 2-(methyl(2-(nicotinamido)ethyl)amino)ethylcarbamate (90 mg, 0.279 mmol) was taken up in a 25% TFA in CH₂Cl₂ solution (5 mL) and allowed to stand at room temperature for 3 h. The reaction mixture was concentrated under reduced pressure to afford the TFA salt of N-(2-((2-aminoethyl)(methyl)amino)ethyl)nicotinamide. This material was taken up in CH₃CN (10 mL) along with (4Z,7Z,10Z,13Z,16Z,19Z)-docosa-4,7,10,13,16,19-hexaenoic acid (90 mg, 0.279 mmol), HATU (117 mg, 0.31 mmol) and DIEA (0.15 mL). The resulting reaction mixture was stirred at room temperature for 2 h. It was then diluted with EtOAc and washed successively with saturated aqueous NaHCO₃ and brine. The organic layer was dried over Na₂SO₄, filtered and concentrated under reduced pressure. Purification by silica gel chromatography (5% MeOH—CH₂Cl₂) afforded N-(2-((2-(4Z,7Z,10Z,13Z,16Z,19Z)-docosa-4,7,10,13,16,19-hexaenamidoethyl)(methyl)amino)ethyl)nicotinamide (30 mg, 20%). MS calculated for $C_{33}H_{48}N_4O_2$: 532.38. found: [M+H]⁺ 533.

Example 8

Preparation of (2S,3R)-methyl 3-((S)-2-((4Z,7Z,10Z,13Z,16Z,19Z)-docosa-4,7,10,13,16,19-hexaenamido)propanoyloxy)-2-(nicotinamido)butanoate (I-9)

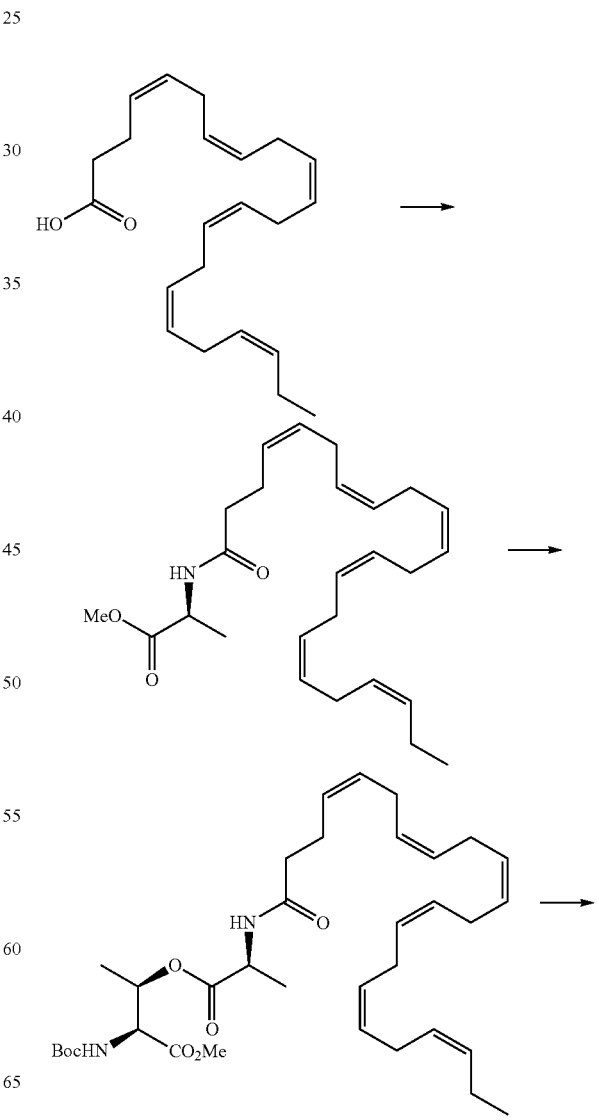

-continued

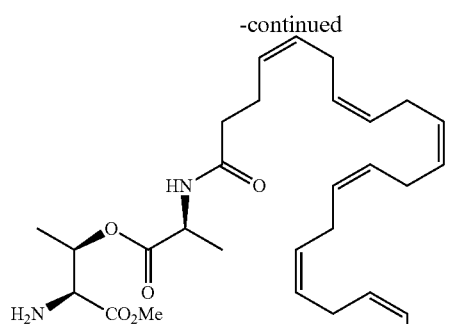

L-Alanine methyl ester hydrochloride (0.85 g, 6.1 mmol) was taken up in CH$_3$CN (20 mL) along with (4Z,7Z,10Z,13Z,16Z,19Z)-docosa-4,7,10,13,16,19-hexaenoic acid (2.0 g, 6.1 mmol), EDCI (1.3 g, 6.72 mmol) and DIEA (1.3 mL). The resulting reaction mixture was stirred at room temperature for 2 h. It was then diluted with EtOAc and washed with dilute aqueous NaHCO$_3$ and brine. The organic layer was dried over Na$_2$SO$_4$, filtered and concentrated under reduced pressure to afford (S)-methyl 2-((4Z,7Z,10Z,13Z,16Z,19Z)-docosa-4,7, 10,13,16,19-hexaenamido)propanoate (2.0 g, 79%).

(S)-methyl 2-((4Z,7Z,10Z,13Z,16Z,19Z)-docosa-4,7,10, 13,16,19-hexaenamido)propanoate (2.0 g, 4.8 mmol) was taken up in THF (8 mL) along with 5M aqueous NaOH (5 mL) and stirred vigorously at room temperature for 3 h. The reaction mixture was diluted with water and concentrated under reduced pressure. Enough 6N HCl was then added to adjust the pH to 2. The resulting mixture was extracted with EtOAc. The combined organic layers were dried over Na$_2$SO$_4$, filtered and concentrated under reduced pressure to afford (S)-2-((4Z,7Z,10Z,13Z,16Z,19Z)-docosa-4,7,10,13,16,19-hexaenamido)propanoic acid. This was taken up in CH$_3$CN (15 mL) along with N-Boc-L-threonine methyl ester (1.11 g, 4.78 mmol), HATU (2.0 g, 5.3 mmol) and DIEA (1.2 mL). The resulting reaction mixture was stirred at room temperature for 6 h and diluted with EtOAc. The organic layer was washed with NaHCO$_3$, brine, dried over Na$_2$SO$_4$, filtered and concentrated under reduced pressure. Purification by silica gel chromatography (CH$_2$Cl$_2$) afforded (2S,3R)-methyl 2-(tert-butoxycarbonyl)-3-(S)-2-((4Z,7Z,10Z,13Z,16Z, 19Z)-docosa-4,7,10,13,16,19-hexaenamido)propanoyloxy) butanoate (1.0 g).

(2S,3R)-methyl 2-(tert-butoxycarbonyl)-3-((S)-2-((4Z, 7Z,10Z,13Z,16Z,19Z)-docosa-4,7,10,13,16,19-hexaenamido)propanoyloxy)butanoate (300 mg, 0.488 mmol) was taken up in 4M HCl in dioxane (2 mL) and allowed to stand at room temperature for 10 min. The reaction mixture was then diluted with EtOAc and concentrated under reduced pressure to afford the HCl salt of (2S,3R)-methyl 2-amino-3-((S)-2-((4Z,7Z,10Z,13Z,16Z,19Z)-docosa-4,7,10,13,16,19-hexaenamido)propanoyloxy)butanoate. This material was taken up in CH$_3$CN (5 mL) along with nicotinic acid (60 mg, 0.488 mmol), HATU (204 mg, 0.54 mmol) and DIEA (0.25 mL, 1.46 mmol). The resulting reaction mixture was stirred at room temperature for 1 h and concentrated under reduced pressure. The resulting oily residue was purified by silica gel chromatography (9:1 CH$_2$Cl$_2$/MeOH) to afford (2S,3R)-methyl 3-((S)-2-((4Z,7Z,10Z,13Z,16Z,19Z)-docosa-4,7,10,13, 16,19-hexaenamido)propanoyloxy)-2-(nicotinamido)butanoate (120 mg, 40%). MS calculated for C$_{36}$H$_{49}$N$_3$O$_6$: 619.36. found: [M+H]$^+$ 620.

Example 9

Preparation of (2S,3R)-methyl 3-((S)-2-((5Z,8Z,11Z, 14Z,17Z)-icosa-5,8,11,14,17-pentaenamido)propanoyloxy)-2-(nicotinamido)butanoate (I-10)

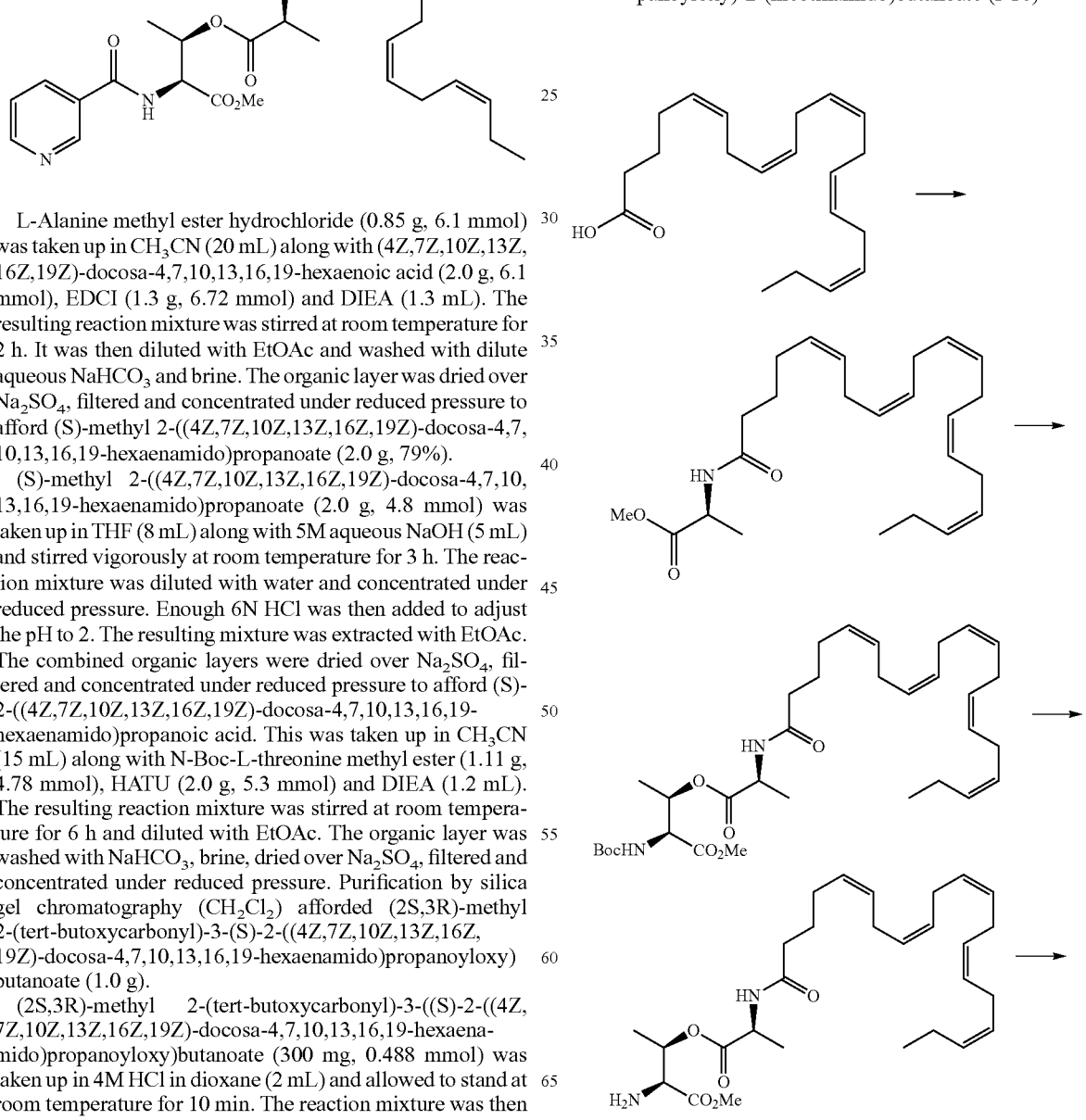

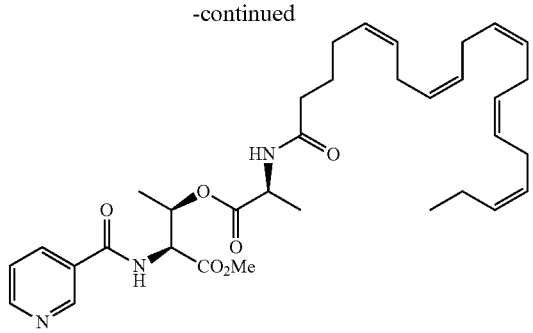

The same synthetic sequence outlined above for the preparation of (2S,3R)-methyl 3-((S)-2-((4Z,7Z,10Z,13Z,16Z,19Z)-docosa-4,7,10,13,16,19-hexaenamido)propanoyloxy)-2-(nicotinamido)butanoate was used, except that (5Z,8Z,11Z,14Z,17Z)-eicosa-5,8,11,14,17-pentaenoic acid (EPA) was used instead of DHA. MS calculated for $C_{34}H_{47}N_3O_6$: 593.35. found: $[M+H]^+$ 594.

Example 10

Preparation of (S)-methyl 6-((4Z,7Z,10Z,13Z,16Z,19Z)-docosa-4,7,10,13,16,19-hexaenamido)-2-(nicotinamido)hexanoate (I-11)

H-Lysine-(BOC)-OMe hydrochloride (500 mg, 1.68 mmol) was taken up in $CH_3CN$ (10 mL) along with nicotinic acid (207 mg, 1.68 mmol), EDCI (354 mg, 1.85 mmol) and DIEA (0.90 mL). The resulting reaction mixture was stirred at room temperature for 18 h and diluted with EtOAc. The organic layer was washed with dilute aqueous $NaHCO_3$, brine, dried over $Na_2SO_4$, filtered and concentrated under reduced pressure. Purification by silica gel chromatography ($CH_2Cl_2$) afforded (5)-methyl 6-(tert-butoxycarbonyl)-2-(nicotinamido)hexanoate (520 mg, 85%).

(S)-Methyl 6-(tert-butoxycarbonyl)-2-(nicotinamido)hexanoate (260 mg, 0.71 mmol) was taken up in 4M HCl in dioxane (2 mL) and allowed to stand at room temperature for 1 h. The reaction mixture was diluted with EtOAc and concentrated under reduced pressure to afford the HCl salt of (5)-methyl 6-amino-2-(nicotinamido)hexanoate. This material was taken up in $CH_3CN$ (5 mL) along with (4Z,7Z,10Z,13Z,16Z,19Z)-docosa-4,7,10,13,16,19-hexaenoic acid (233 mg, 0.71 mmol), HATU (297 mg, 0.78 mmol) and DIEA (0.4 mL). The resulting reaction mixture was stirred at room temperature for 2 h and diluted with EtOAc. The organic layer was washed with dilute aqueous $NaHCO_3$, brine, dried over $Na_2SO_4$, filtered and concentrated under reduced pressure. Purification by silica gel chromatography (9:1 $CH_2Cl_2$/MeOH) afforded (S)-methyl 6-((4Z,7Z,10Z,13Z,16Z,19Z)-docosa-4,7,10,13,16,19-hexaenamido)-2-(nicotinamido) hexanoate (280 mg, 72%). MS calculated for $C_{35}H_{49}N_3O_4$: 575.37. found: $[M+H]^+$ 576.

Example 11

Preparation of (S)-6-((4Z,7Z,10Z,13Z,16Z,19Z)-docosa-4,7,10,13,16,19-hexaenamido)-2-(nicotinamido)hexanoic acid (I-12)

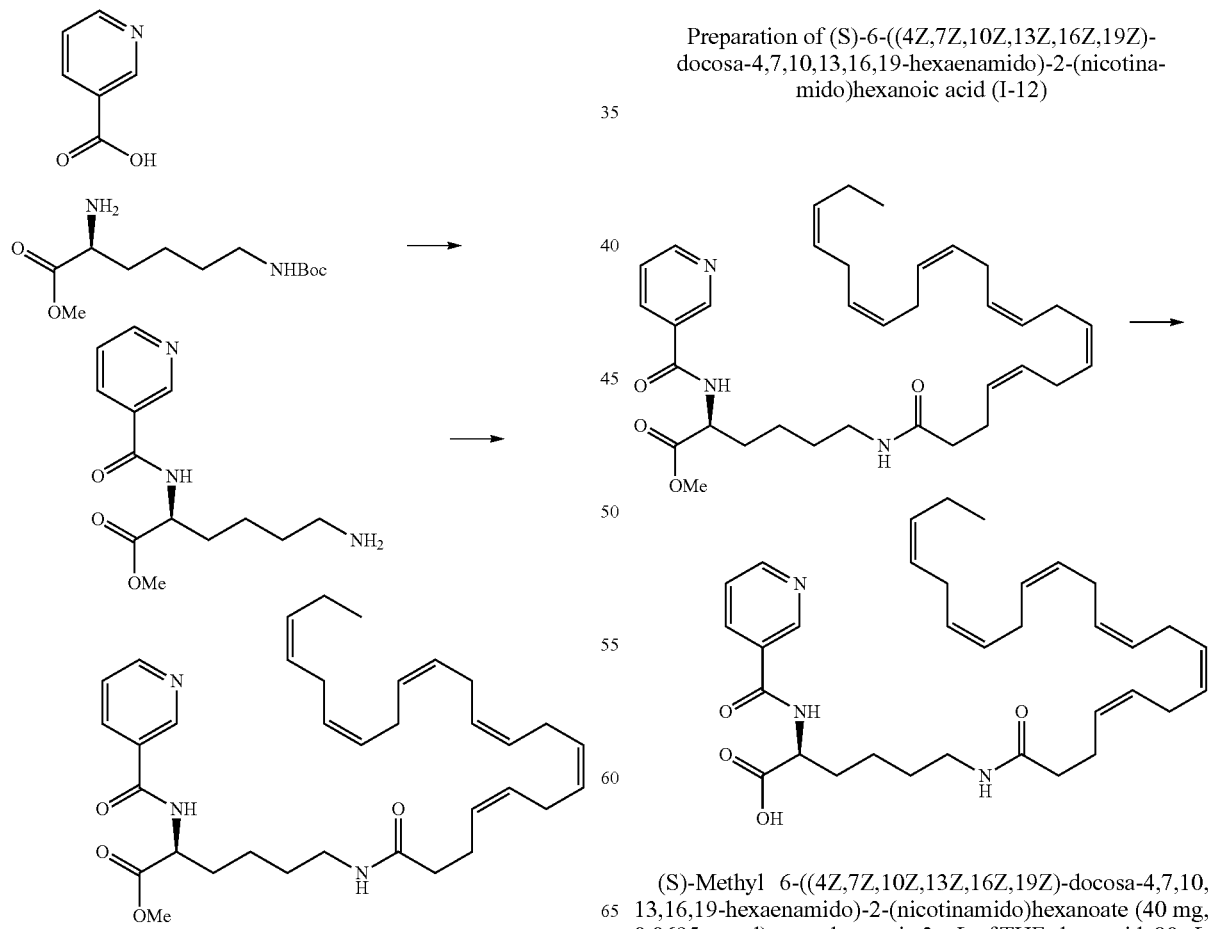

(S)-Methyl 6-((4Z,7Z,10Z,13Z,16Z,19Z)-docosa-4,7,10,13,16,19-hexaenamido)-2-(nicotinamido)hexanoate (40 mg, 0.0695 mmol) was taken up in 2 mL of THF along with 80 μL of a 5 M NaOH solution. The resulting reaction mixture was stirred at room temperature for 2 h. It was then acidified to pH 4 with 2 N HCl and then extracted with EtOAc. The combined organic layers were dried (Na$_2$SO$_4$) and concentrated under reduced pressure to afford 31 mg of (S)-6-((4Z,7Z,10Z,13Z,16Z,19Z)-docosa-4,7,10,13,16,19-hexaenamido)-2-(nicotinamido)hexanoic acid. MS calculated for C$_{34}$H$_{47}$N$_3$O$_4$: 561.36. found: [M+H]$^+$ 562.

Example 12

Preparation of (S)-methyl 2-((5Z,8Z,11Z,14Z,17Z)-eicosa-5,8,11,14,17-pentaenamido)-6-(nicotinamido)hexanoate (I-13)

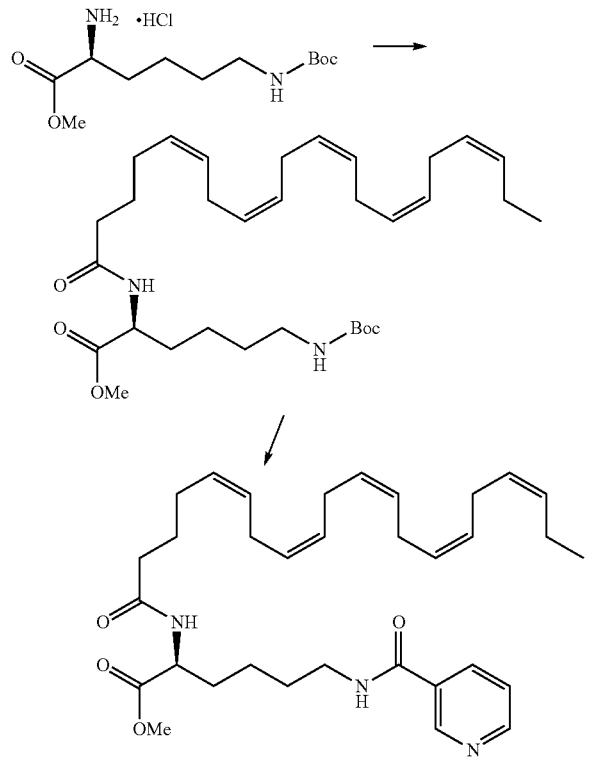

H-Lysine-(BOC)—OMe hydrochloride (500 mg, 1.68 mmol) was taken up in 25 mL of CH$_3$CN along with (5Z,8Z,11Z,14Z,17Z)-eicosa-5,8,11,14,17-pentaenoic acid (EPA, 509 mg, 1.68 mmol), HATU (702 mg, 1.85 mmol) and DIEA (880 µL, 5.04 mmol). The resulting reaction mixture was stirred at room temperature for 2 h. It was then diluted with EtOAc (70 mL) and washed with brine (20 mL). The organic layer was dried (Na$_2$SO$_4$) and concentrated under reduced pressure. The resulting residue was purified by silica gel chromatography (CH$_2$Cl$_2$, gradient elution to 90% CH$_2$Cl$_2$, 10% MeOH) to afford 870 mg of (S)-methyl 6-(tert-butoxycarbonyl)-2-((5Z,8Z,11Z,14Z,17Z)-eicosa-5,8,11,14,17-pentaenamido)hexanoate (95% yield). MS calculated for C$_{32}$H$_{52}$N$_2$O$_5$: 544.39. found: [M+H]$^+$ 545.

(S)-Methyl 6-(tert-butoxycarbonyl)-2-((5Z,8Z,11Z,14Z,17Z)-eicosa-5,8,11,14,17-pentaenamido)hexanoate (870 mg, 1.60 mmol) was taken up in 4 mL of 4 N HCl in dioxane and allowed to stand at room temperature for 10 min. The reaction mixture was diluted with 10 mL of EtOAc and concentrated under reduced pressure to afford the HCl salt of (S)-methyl 6-amino-2-((5Z,8Z,11Z,14Z,17Z)-eicosa-5,8,11,14,17-pentaenamido)hexanoate. This residue was taken up in 5 mL of CH$_3$CN along with nicotinic acid (197 mg, 1.60 mmol), HATU (669 mg, 1.76 mmol) and DIEA (836 mL, 4.8 mmol). The resulting reaction mixture was stirred at room temperature for 2 h and diluted with EtOAc (20 mL). The organic layer was washed with brine (20 mL), dried (Na$_2$SO$_4$) and concentrated under reduced pressure. The resulting residue was purified by chromatography (95% CH$_2$Cl$_2$, 5% MeOH) to afford 300 mg of (S)-methyl 2-((5Z,8Z,11Z,14Z,17Z)-eicosa-5,8,11,14,17-pentaenamido)-6-(nicotinamido)hexanoate. MS calculated for C$_{33}$H$_{47}$N$_3$O$_4$: 549.36. found: [M+H]$^+$ 550.

Example 13

Preparation of (S)-2-((5Z,8Z,11Z,14Z,17Z)-eicosa-5,8,11,14,17-pentaenamido)-6-(nicotinamido)hexanoic acid (I-14)

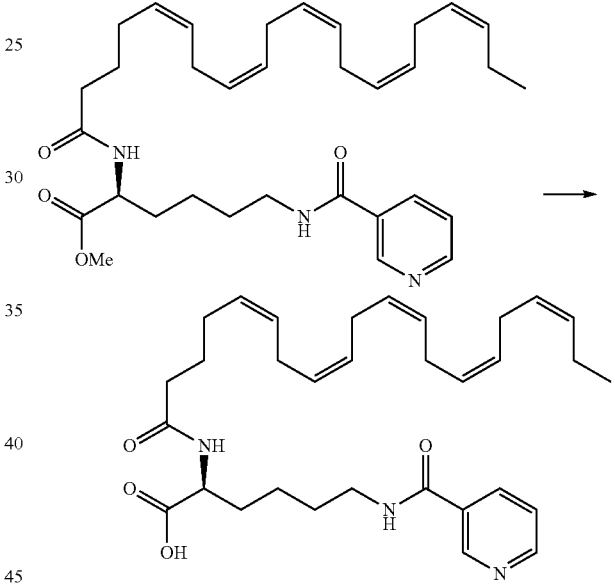

(S)-methyl 2-((5Z,8Z,11Z,14Z,17Z)-eicosa-5,8,11,14,17-pentaenamido)-6-(nicotinamido)hexanoate (140 mg, 0.225 mmol) was taken up in 2 mL of THF along with an aqueous solution of NaOH (35 mg in 2 mL of H$_2$O). The resulting reaction mixture was stirred at room temperature for 2 h. It was then acidified to pH 4 with 2 N HCl and then extracted with EtOAc. The combined organic layers were dried (Na$_2$SO$_4$) and concentrated under reduced pressure to afford 31 mg of (S)-2-((5Z,8Z,11Z,14Z,17Z)-eicosa-5,8,11,14,17-pentaenamido)-6-(nicotinamido)hexanoic acid. MS calculated for C$_{34}$H$_{47}$N$_3$O$_4$: 561.36. found: [M+H]$^+$ 562. MS calculated for C$_{32}$H$_{45}$N$_3$O$_4$: 535.34. found: [M+H]$^+$ 536.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

Example 14

Preparation of 3-((4Z,7Z,10Z,13Z,16Z,19Z)-docosa-4,7,10,13,16,19-hexaenoyloxy)ethyl nicotinoate

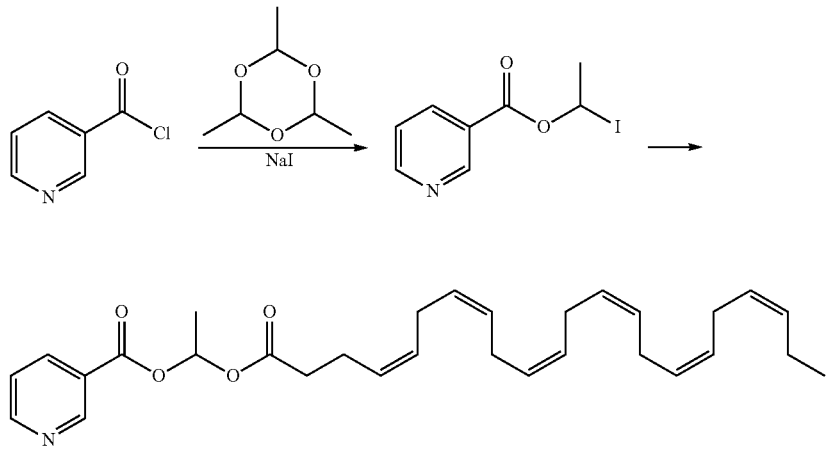

In a typical run, nicotinic acid is dissolved in $CH_2Cl_2$ and to this mixture is added oxalyl chloride. After a few drops of DMF are added, the reaction mixture is stirred at room temperature until all the solids have dissolved and all gas evolution has ceased (1 h). This freshly prepared solution of the acid chloride is added dropwise at 0° C. to a solution containing 2,4,6-trimethyl-1,3,5-trioxane and NaI in $CH_2Cl_2$. The resulting reaction mixture is warmed to room temperature and is stirred for 16 h. It is then filtered and concentrated under reduced pressure. Purification by silica gel chromatography ($CH_2Cl_2$) affords 3-iodoethylnicotinoate.

To a solution of DHA in $CH_3CN$ is added $K_2CO_3$ followed by the addition of $Bu_4NBr$. The mixture is stirred and cooled to 0° C. 3-Iodoethylnicotinoate is then added and the mixture is stirred (RT, 16 h). The mixture is filtered, washed with brine and concentrated under reduced pressure. The crude product is purified by silica chromatography to afford 3-((4Z,7Z,10Z, 13Z,16Z,19Z)-docosa-4,7,10,13,16,19-hexaenoyloxy)ethyl nicotinoate.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:
1. A compound of Formula I:

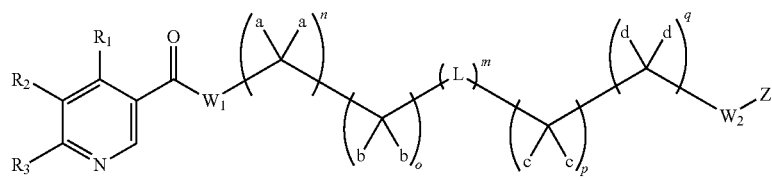

Formula I or a pharmaceutically acceptable salt, enantiomer or stereoisomer thereof;
wherein
$R_1$, $R_2$, and $R_3$ are each independently selected from the group consisting of —H, -D, —Cl, —F, —CN, —$NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —C(O)H, —C(O)$C_1$-$C_3$ alkyl, —C(O)O$C_1$-$C_3$ alkyl, —C(O)$NH_2$, —C(O)NH($C_1$-$C_3$ alkyl), —C(O)N($C_1$-$C_3$ alkyl)$_2$, —$C_1$-$C_3$ alkyl, —O—$C_1$-$C_3$ alkyl, —S(O)$C_1$-$C_3$ alkyl, and —S(O)$_2$$C_1$-$C_3$ alkyl;

$W_1$ and $W_2$ are each NR;

each a, b, c, and d is independently —H, -D, Halogen, —$CH_3$, —$OCH_3$, —$OCF_3$, —$OCH_2CH_3$, or —C(O) OR, —O—Z, or benzyl, or two of a, b, c, and d can be taken together along with the single carbon to which they are bound to form a cycloalkyl or heterocycle;

each n, o, p, and q is independently 0 or 1;

each L is independently —O—, —S—, —S(O)—, —S(O)$_2$—, —S—S—,

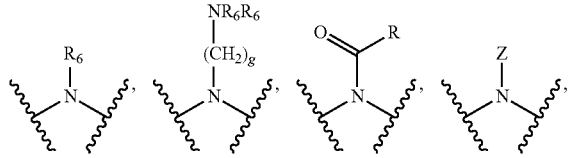

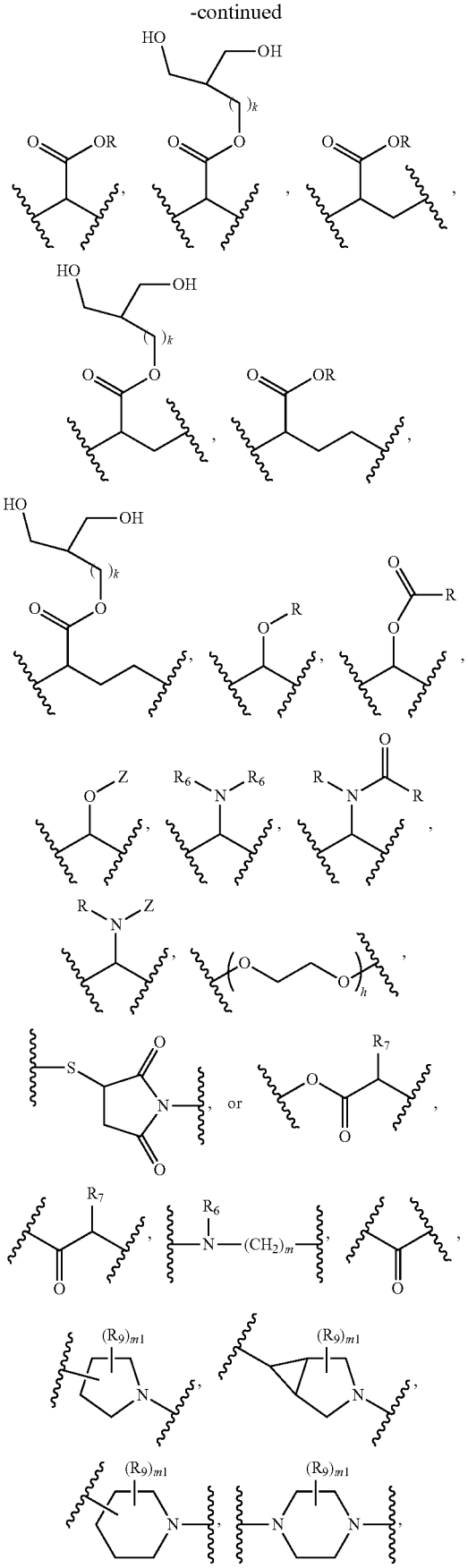
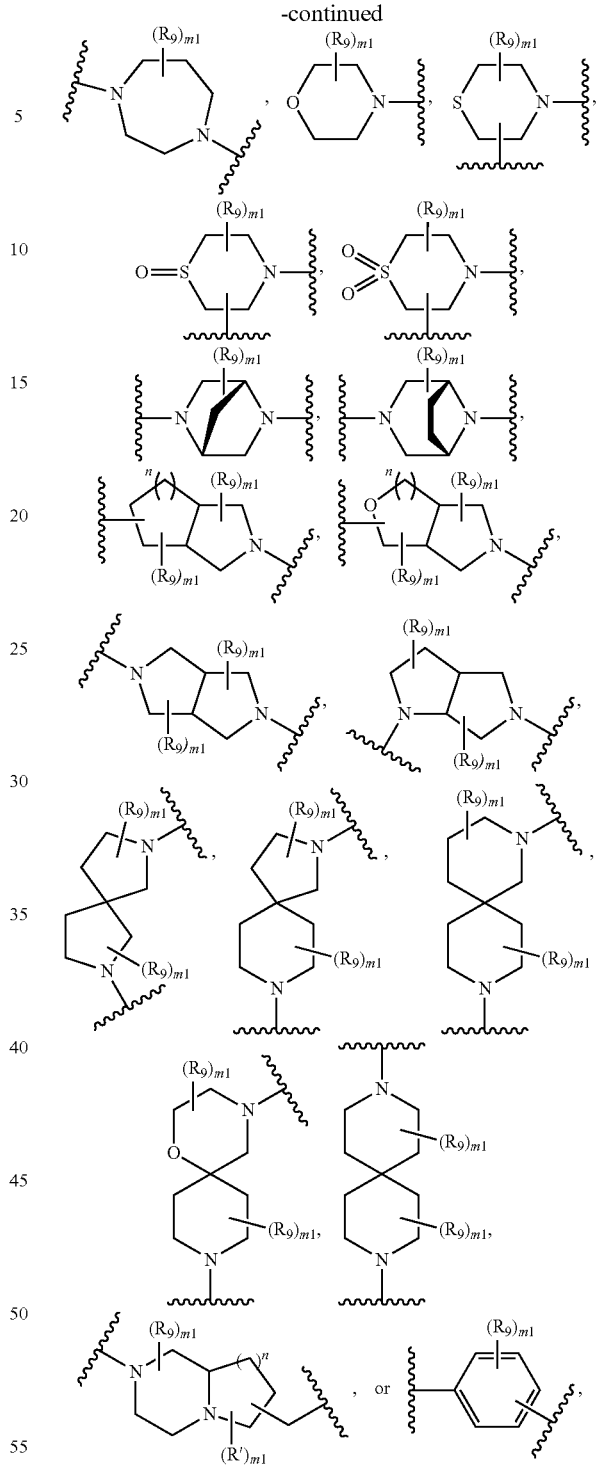
each g is independently 2, 3 or 4;
each h is independently 1, 2, 3 or 4;
each m is independently 0, 1, 2, or 3; if m is more than 1, then L can be the same or different;
each m1 is independently 0, 1, 2, or 3;
k is 0, 1, 2, or 3;
each $R_6$ is independently H or $C_1$-$C_6$ alkyl, or both $R_6$ groups, when taken together with the nitrogen to which they are attached, can form a heterocycle;

each $R_7$ is independently e, H or straight or branched $C_1$-$C_{10}$ alkyl which can be optionally substituted with OH, $NH_2$, $CO_2R$, $CONH_2$, phenyl, $C_6H_4OH$, imidazole or arginine;

each e is independently H or any one of the side chains of the naturally occurring amino acids;

each $R_9$ is independently —H, -D, $C_1$-$C_4$ alkyl, halogen, cyano, oxo, thiooxo, —OH, $C(O)C_1$-$C_4$ alkyl, O-aryl, O-benzyl, $OC(O)C_1$-$C_4$ alkyl, $C_1$-$C_3$ alkene, $C_1$-$C_3$ alkyne, $C(O)C_1$-$C_4$ alkyl, $NH_2$, $NH(C_1$-$C_3$ alkyl), $N(C_1$-$C_3$ alkyl)$_2$, $NH(C(O)C_1$-$C_3$ alkyl), $N(C(O)C_1$-$C_3$ alkyl)$_2$, SH, $S(C_1$-$C_3$ alkyl), $S(O)C_1$-$C_3$ alkyl, $S(O)_2C_1$-$C_3$ alkyl;

each Z is independently —H,

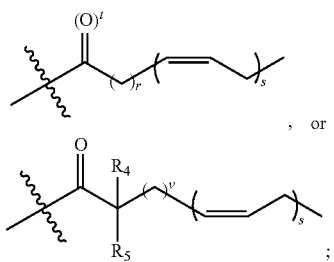
, or

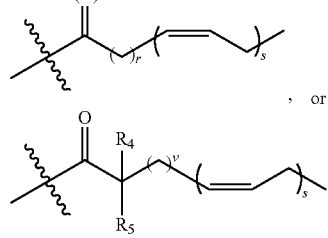
;

with the proviso that there is at least one

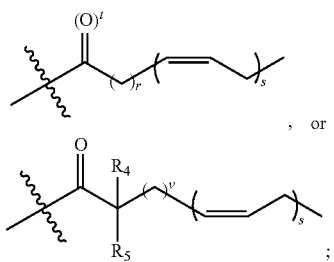
, or

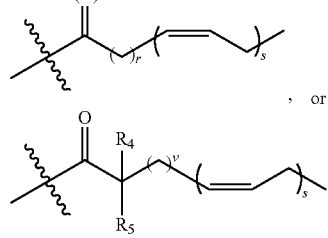

each r is independently 2, 3, or 7;
each s is independently 3, 5, or 6;
each t is independently 0 or 1;
each v is independently 1, 2, or 6;
$R_4$ and $R_5$ are each independently hydrogen, deuterium, —$C_1$-$C_4$ alkyl, -halogen, —OH, —$C(O)C_1$-$C_4$ alkyl, —O-aryl, —O-benzyl, —$OC(O)C_1$-$C_4$ alkyl, —$C_1$-$C_3$ alkene, —$C_1$-$C_3$ alkyne, —$C(O)C_1$-$C_4$ alkyl, —$NH_2$, —$NH(C_1$-$C_3$ alkyl), —$N(C_1$-$C_3$ alkyl)$_2$, —$NH(C(O)C_1$-$C_3$ alkyl), —$N(C(O)C_1$-$C_3$ alkyl)$_2$, —SH, —$S(C_1$-$C_3$ alkyl), —$S(O)C_1$-$C_3$ alkyl, —$S(O)_2C_1$-$C_3$ alkyl; and
each R is independently —H, or straight or branched $C_1$-$C_4$ alkyl optionally substituted with OR, $NR_2$, or halogen.

2. The compound of claim 1, wherein Z is

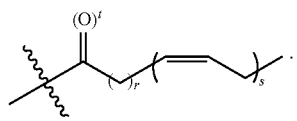

3. The compound of claim 2, wherein t is 1.
4. The compound of claim 3, wherein r is 2 and s is 6.
5. The compound of claim 3, wherein r is 3 and s is 5.
6. The compound of claim 3, wherein r is 7 and s is 3.
7. The compound of claim 4, wherein L is —S—S—.
8. The compound of claim 4, wherein L is —O—.
9. The compound of claim 4, wherein L is

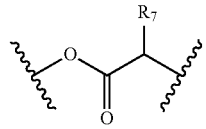

10. The compound of claim 4, wherein L is

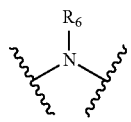

11. The compound of claim 4, wherein L is

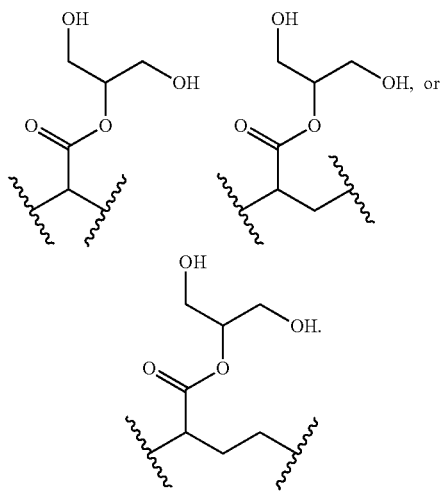

12. The compound of claim 4, wherein L is

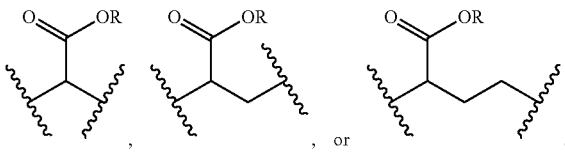

13. The compound of claim 4, wherein one of n, o, p, and q are each 1.

14. The compound of claim 4, wherein two of n, o, p, and q are each 1.

15. The compound of claim 4, wherein m is 1, n, o, p, and q are each 1, and L is O.

16. The compound of claim 5, wherein m is 1, n, o, p, and q are each 1, and L is —S—S—.

17. The compound of claim 4, wherein m, n, and o are each 0, and p and q are each 1.

18. The compound of claim 4, wherein m is 1, n, o, p, and q are each 0, and L is

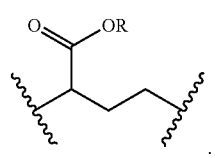

19. The compound of claim 4, wherein m is 1, n and o are each 1, p and q are each 0, and L is

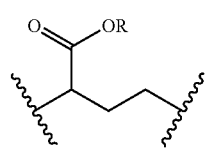

20. The compound of claim 4, wherein m is 1, n, o, p, and q are each 1, and L is

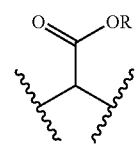

21. The compound of claim 4, wherein m is 1, n, o, p, and q are each 1, and L is $NR_6$.

22. The compound of claim 4, wherein m is 1, n and o are each 1, p and q are each 0, and L is

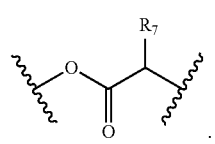

23. A pharmaceutical composition comprising a compound of claim 1 and a pharmaceutically acceptable carrier.

24. The compound of claim 5, wherein L is —S—S—.

25. The compound of claim 5, wherein L is —O—.

26. The compound of claim 5, wherein L is

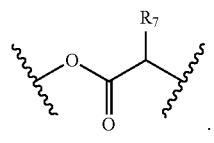

27. The compound of claim 5, wherein L is

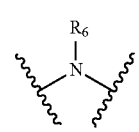

28. The compound of claim 5, wherein L is

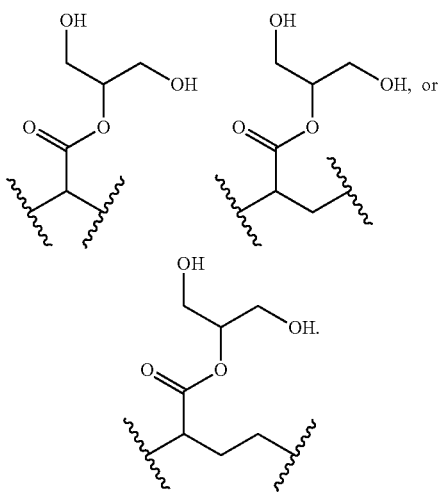

29. The compound of claim 5, wherein L is

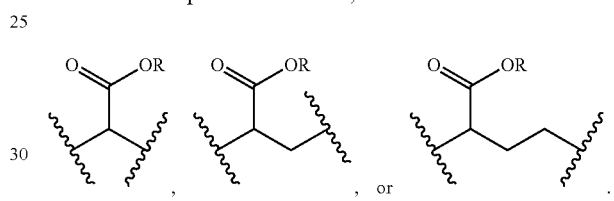

30. The compound of claim 5, wherein one of n, o, p, and q is 1.

31. The compound of claim 5, wherein two of n, o, p, and q are each 1.

32. The compound of claim 5, wherein m is 1, n, o, p, and q are each 1, and L is O.

33. The compound of claim 5, wherein m is 1, n, o, p, and q are each 1, and L is —S—S—.

34. The compound of claim 5, wherein m, n, and o are each 0, and p and q are each 1.

35. The compound of claim 5, wherein m is 1, n, o, p, and q are each 0, and L is

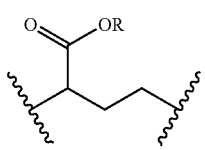

36. The compound of claim 5, wherein m is 1, n and o are each 1, p and q are each 0, and L is

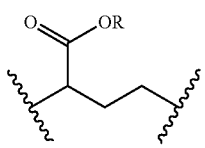

37. The compound of claim 5, wherein m is 1, n, o, p, and q are each 1, and L is
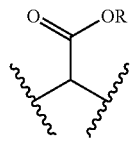
38. The compound of claim 5, wherein m is 1, n, o, p, and q are each 1, and L is $NR_6$.
39. The compound of claim 5, wherein m is 1, n and o are each 1, p and q are each 0, and L is
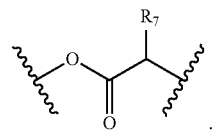
40. The compound of claim 5, wherein m is 0, n, o, are each 1, p and q are each 0, and a and b are each —H.
* * * * *